US009486169B1

(12) United States Patent
Ahmad

(10) Patent No.: US 9,486,169 B1
(45) Date of Patent: Nov. 8, 2016

(54) KETONE MEASUREMENT SYSTEM AND RELATED METHOD WITH ACCURACY AND REPORTING ENHANCEMENT FEATURES

(71) Applicant: Invoy Technologies, L.L.C., Chandler, AZ (US)

(72) Inventor: Lubna M. Ahmad, Chandler, AZ (US)

(73) Assignee: Invoy Technologies, LLC, Aliso Viejo, CA (US)

(*) Notice: Subject to any disclaimer, the term of this patent is extended or adjusted under 35 U.S.C. 154(b) by 0 days.

(21) Appl. No.: 14/690,756

(22) Filed: Apr. 20, 2015

Related U.S. Application Data

(60) Provisional application No. 61/981,484, filed on Apr. 18, 2014.

(51) Int. Cl.

| | |
|---|---|
| *G01N 33/48* | (2006.01) |
| *A61B 5/00* | (2006.01) |
| *A61B 5/145* | (2006.01) |
| *A61B 5/0205* | (2006.01) |
| *G01N 33/497* | (2006.01) |
| *G01N 33/49* | (2006.01) |
| *G01N 33/64* | (2006.01) |
| *A61B 5/08* | (2006.01) |

(52) U.S. Cl.
CPC ........... *A61B 5/6898* (2013.01); *A61B 5/0004* (2013.01); *A61B 5/0205* (2013.01); *A61B 5/14546* (2013.01); *G01N 33/49* (2013.01); *G01N 33/497* (2013.01); *G01N 33/64* (2013.01); *A61B 5/082* (2013.01); *A61B 5/4866* (2013.01); *A61B 2562/0295* (2013.01)

(58) Field of Classification Search
CPC .................................................. A61B 5/4866
USPC ......................................................... 702/19
See application file for complete search history.

(56) References Cited

U.S. PATENT DOCUMENTS

| | | | |
|---|---|---|---|
| 4,931,404 A | 6/1990 | Kundu | |
| 5,071,769 A | 12/1991 | Kundu | |
| 5,174,959 A | 12/1992 | Kundu et al. | |
| 5,788,674 A | 8/1998 | McWilliams | |
| 5,975,078 A | 11/1999 | Pauley | |
| 6,609,068 B2 | 8/2003 | Cranley et al. | |
| 7,364,551 B2 | 4/2008 | Allen et al. | |
| 7,373,820 B1 | 5/2008 | James | |
| 7,704,227 B2 | 4/2010 | Moberg et al. | |
| 7,727,369 B2 | 6/2010 | Kühn | |
| 8,036,708 B2 | 10/2011 | Oozeki | |
| 8,221,345 B2 | 7/2012 | Blomquist | |
| 8,280,436 B2 | 10/2012 | Harris, Jr. | |
| 8,644,760 B2 | 2/2014 | Tuikka | |
| 8,871,521 B2 | 10/2014 | Akers, Jr. | |
| 2003/0161744 A1 | 8/2003 | Vilks et al. | |
| 2003/0208133 A1* | 11/2003 | Mault | A61B 5/0002 600/532 |
| 2004/0236244 A1 | 11/2004 | Allen et al. | |
| 2005/0151813 A1 | 7/2005 | Ikezaki | |
| 2006/0173260 A1 | 8/2006 | Gaoni et al. | |
| 2007/0078370 A1 | 4/2007 | Shener et al. | |
| 2007/0173711 A1 | 7/2007 | Shah et al. | |
| 2007/0254593 A1 | 11/2007 | Jollota et al. | |
| 2008/0053194 A1 | 3/2008 | Ahmad | |
| 2008/0077026 A1 | 3/2008 | Banet et al. | |
| 2009/0054799 A1 | 2/2009 | Vrtis et al. | |
| 2009/0118594 A1 | 5/2009 | Zdeblick | |
| 2009/0270705 A1 | 10/2009 | Enegren et al. | |
| 2009/0315667 A1 | 12/2009 | Kawamura et al. | |
| 2010/0010443 A1 | 1/2010 | Morgan et al. | |
| 2011/0028091 A1 | 2/2011 | Higgins et al. | |
| 2011/0063094 A1 | 3/2011 | Meiertoberens et al. | |
| 2011/0178462 A1 | 7/2011 | Moberg et al. | |
| 2011/0308019 A1 | 12/2011 | Terawaki et al. | |
| 2013/0096399 A1 | 4/2013 | Scalici et al. | |
| 2013/0102018 A1 | 4/2013 | Schentag et al. | |
| 2013/0154917 A1 | 6/2013 | Adermann et al. | |
| 2013/0231711 A1* | 9/2013 | Kaib | G06F 19/3418 607/5 |
| 2014/0112227 A1 | 4/2014 | Hasegawa | |
| 2014/0148757 A1 | 5/2014 | Ambrosina et al. | |
| 2014/0235171 A1 | 8/2014 | Molettiere et al. | |

(Continued)

FOREIGN PATENT DOCUMENTS

| | | |
|---|---|---|
| WO | WO 2013/164836 | 11/2013 |
| WO | WO 2014/158365 | 10/2014 |

OTHER PUBLICATIONS

Abbott Laboratories Breath Acetone Analyzer Section 501(k) Notification, Nov. 30, 1987. (Part 1 of 3).
Abbott Laboratories Breath Acetone Analyzer Section 501(k) Notification, Nov. 30, 1987. (Part 2 of 3).
Abbott Laboratories Breath Acetone Analyzer Section 501(k) Notification, Nov. 30, 1987. (Part 3 of 3).
Accu-Chek Aviva Combo Advanced Owner's Booklet for Self-Testing Only, Jul. 2012. (Part 1 of 2).
Accu-Chek Aviva Combo Advanced Owner's Booklet for Self-Testing Only, Jul. 2012. (Part 2 of 2).

(Continued)

*Primary Examiner* — Jerry Lin
(74) *Attorney, Agent, or Firm* — Knobbe, Martens, Olson & Bear, LLP

(57) ABSTRACT

A portable ketone measurement device measures ketone levels in breath samples or other bodily fluid samples of a user, and communicates the ketone measurements to an application that runs on a smartphone or other mobile device of the user. The application may communicate with, and report the measurements to, a remote server. One or more components of the system (e.g., the portable ketone measurement device, the mobile application, and/or the server) may, where appropriate, adjust the ketone measurements to compensate for ketone variations resulting from, e.g., the age of the user, a medical condition of the user, a missed medication event, or an interrupted sleep event. The application may, in some scenarios, withhold the display of a ketone measurement from the user until an authorization has been received from the server.

37 Claims, 17 Drawing Sheets

(56) References Cited

U.S. PATENT DOCUMENTS

2014/0275876 A1 9/2014 Hansen et al.
2014/0276100 A1 9/2014 Satterfield et al.
2014/0377877 A1 12/2014 Burgi et al.

OTHER PUBLICATIONS

Chakraborty et al., "Detection of biomarker in breath: A step towards noninvasive diabetes monitoring," Current Science, vol. 94, pp. 237-242, Sep. 25, 2008.
CMS Operator Guide, http://www.buydraegertubes.com/ds/cms-ops-guide.pdf, Apr. 19, 2002.
Diskin et al., "Time variation of ammonia, acetone, isoprene and ethanol in breath: a quantitative SIFT-MS study over 30 days," 24 Physiol. Meas. 107, 107-119 (2003).
Dräger CMS Product Information, http://www.draeger.com/sites/assets/PublishingImages/Products/cin_chip_measurement_system/US/cms-ds-pi-9044337-en-us.pdf (document properties of document indicate that the document was created on Dec. 1, 2008).
DrägerTubes & accuro Pump Product Information, http://www.draeger.com/sites/assets/PublishingImages/Products/cin_accuro/US/081209-pi-DetectorTubes-22-10-2008-en.pdf (document properties of document indicate that the document was created on Nov. 11, 2008).
Ketonix 2015 Blue Specifications, https://www.ketonix.com/index.php/product-2/ketonix-2015-blue, 2015.
Ketonix data for Michel Lundell, https://www.ketonix.com, 2015.
Kinoyama et al., "Acetone and Isoprene Concentrations in Exhaled Breath in Healthy Subjects," 54(4) Journal of Health Science 471, 471-477 (2008).
Kundu et al., "Breath Acetone Analyzer: Diagnostic Tool to Monitor Dietary Fat Loss," 39/1 Clin. Chem. 87, 87-92 (1993).
Kupari et al., "Breath Acetone in Congestive Heart Failure," 76 The American Journal of Cardiology 1076, 1076-1078 (Nov. 15, 1995).
Landini et al., "Breath Acetone Concentration Measured Using a Palm-Size Enzymatic Sensor System," 9 IEEE Sensors Journal 1802, 1802-1807 (Dec. 2009).
Landini et al., "Effect of Exhalation Variables on the Current Response of an Enzymatic Breath Acetone Sensing Device," 10 IEEE Sensors Journal 19, 19-24 (Jan. 2010).
MiniMed 530G System User Guide, 2012.
Musa-Veloso et al., "Breath acetone is a reliable indicator of ketosis in adults consuming ketogenic meals," 76 Am. J. Clin. Nutr. 65, 65-70 (2002).
Schwarz et al., "Breath acetone-aspects of normal physiology related to age and gender as determined in a PTR-MS study," 3 Journal of Breath Research 1, 1-9 (2009).
Yamada et al., "Breath Acetone Analyzer to Achieve 'Biochip Mobile Terminal,'" *NTT DOCOMO Technical Journal*, vol. 14, pp. 51-57, 2012.

\* cited by examiner

| Measurement Device | COMM Device (POCED) | Remote System |
|---|---|---|
| 1. User powers up Measurement Device (MD), MD automatically boots up and initializes itself. User configures the MD as needed. | | |
| | 2. User powers up the POCED and calls up Software App, Software App initializes POCED, Establishes comm with MD, and displays "Ready." | |
| 3. User inputs the fluid sample into the MD and selects "Run Test." The MD conducts the ketone measurement by measuring the ketone concentration, generating a measurement signal, and automatically transmitting the measurement signal to the POCED. | | |
| | 4. The POCED receives the measurement signal and automatically analyzes or processes the measurement signal, modifies the measurement signal as appropriate to compensate for known or reasonably predictable effects of variables, and transmits the measurement signal as modified to the Remote System. | |
| | | 5. The Remote System receives the measurement signal as modified and stores it. The Remote System optionally may transmit a confirmation to the POCED, and optionally may further analyze or process the measurement signal. |

FIG. 3

KETONE MEASUREMENT SYSTEM AND RELATED METHOD WITH ACCURACY AND REPORTING ENHANCEMENT FEATURES

CROSS REFERENCE TO RELATED APPLICATIONS

This application claims the benefit of priority to U.S. Provisional Application 61/981,484, filed Apr. 18, 2014, which is incorporated by reference herein in its entirety.

FIELD OF THE INVENTION

The invention relates generally to devices, systems and methods for measuring one or more analytes in blood, urine and/or breath, preferably endogenous analytes in human blood, urine and/or breath but others as well.

BACKGROUND OF THE INVENTION

Potential benefits of devices, systems and methods for measurement of chemical components or "analytes" in breath are known. Measurement of breath historically, however, has been done using relatively large and expensive laboratory equipment in a controlled lab or clinical setting. Recently there has been a drive to increase the feasibility and practicality of measuring breath by lowering equipment size, requirements, logistics and costs. The assignee of the present invention, for example, has developed a line of small, portable, relatively inexpensive and yet highly-accurate breath acetone analysis devices that reliably measure breath acetone in the low concentrations typically encountered in health and medical applications.

The state of the art in breath analysis has generally been directed towards the development of specific and selective sensors to quantify analytes—usually a single analyte—in breath. Individuals skilled in the art typically come from varying backgrounds of bioinstrumentation, chemistry, and physiology. Innovation in this industry has been further restricted by federal regulations. Such requirements often direct developers towards accepted thinking paradigms and often restrict or disincentivize cross-disciplinary efforts, especially those with unregulated industries, such as software, gaming, and artificial intelligence. Accordingly, there are substantial aspects of linkage between breath analysis devices and storage or centralized databases that are previously underdeveloped. As an example, there is no centralized information regarding the output of breath analyzers that facilitates bi-directional communication with the user for enhanced reporting.

Innovation in breath analysis is further challenged by the paucity of clinical relevance data, i.e., data establishing the relevance of the particular technology and the willingness of the applicable clinical community to adopt it. Although it is often cited that there are on the order of 300 analytes present in human breath, few (e.g., perhaps around ten) are generally clinically recognized. Procuring clinical relevance data is difficult, from the perspective of time, effort and money. Gas analysis tools, such as selected ion flow tube mass spectroscopy (SIFT-MS) and gas chromatography and mass spectroscopy (GC-MS), require large capital expenditures and trained technicians, which substantially reduce the volume of data that is available. The state of the art, therefore, is directed towards building devices that measure breath analytes (again, typically a single analyte) within a hypothesized analyte concentration range that one expects to encounter when the analyte measurement is made in a clinical context.

Ketone measurement has been studied but, as with breath analysis, has been primarily restricted to laboratory analysis. In recent years, point-of-care ketone analyzers, e.g., urine dipstick tests, have been commercially introduced, but those tests have been performed on a one-off basis, typically for preventing diabetic complications, e.g., such as diabetic ketoacidosis, perhaps 8-12 times per year. Systems and methods are needed that enable management of ketone data sets that are collected on a much more frequent basis, e.g., daily or multi-daily, such as 365 to 730 times a year. The significant increase in the number of measurements necessitates superior analysis and interpretation techniques.

Without the existence of commercially-viable and widely-deployed breath analysis devices, solutions directed to optimizing user interface, user feedback, clinical relevance and others have yet to be provided.

Breath analysis also has been limited in that multiple variables can affect the measurement results. Given the relative newness of the field and the relative paucity of commercial devices available for breath analysis, little attention has been paid to the variance of measurements and the variables that affect or give rise to those variances.

SUMMARY OF THE INVENTION

In accordance with one aspect of the invention, a system is provided for measuring a ketone in a fluid of a user. The system comprises a portable measurement device that measures the ketone at a first location and generates a measurement signal indicative of the concentration of the ketone in the fluid, a communications device located at the first location and in operative communication with the measurement device that receives the measurement signal and transmits the measurement signal, and a remote system disposed at a second location remote from the first location that receives the measurement signal from the communications device. At least one of the measurement device, the communications device and the remote system comprises at least one processor that processes parameter data and generates a compensation factor for effecting a modification of the measurement signal to compensate for a compensation variable.

The measurement device may a blood ketone measurement device, a urine ketone measurement device, a breath ketone measurement device, and combinations of these.

The communications device may comprises a wireless telecommunications device such as a cellular phone, a smart phone, a general purpose smart phone, and the like. Such devices preferably comprise a software application that receives the measurement signal from the measurement device and uses at least one processor to process the parameter data to obtain the compensation factor.

The remote system is located at a remote facility, the latter of which may comprise a health care facility, a health care monitoring facility, and the like.

The parameter data may comprise user-specific data, for example, such as lifestyle data, physical data, pathophysiological data and the like. The user-specific data also may comprise at least one of use by the user of medication, alcohol and tobacco. It also may comprise physical activity of the user, food intake of the user, and the like.

The parameter data also may comprise measurement device data, measurement data, measurement state data, and combinations of these. The measurement data may comprise a fluid sample collection protocol, a sensing protocol, a processing protocol, and combinations of these.

The parameter data also may comprise environmental data, baseline data, normal state data, and the like.

The at least one of the measurement device, the communications device and the remote system that comprises the at least one processor may the measurement device, the communications device, the remote system, and combinations of these. The measurement device may comprise storage that pre-stores a portion of the parameter data, for example, in the form of measurement device data, measurement data, or combinations of these.

The communications device similarly may comprise storage that pre-stores a portion of the parameter data. In this event, the communications device storage preferably pre-stores the portion of the parameter data in the form of user-specific data, environmental data, and combinations of these.

The remote system also may comprise storage that pre-stores a portion of the parameter data, for example, such as population data, environmental data, and combinations of these.

Preferably the measurement device automatically transmits the measurement signal to the communications device upon generation of the measurement signal. It is also preferred that the communications device automatically transmits the measurement signal to the remote system upon receiving the measurement signal from the measurement device. Optionally, the communications device, upon receiving the measurement signal from the measurement device, may withhold the transmission of the measurement signal to the remote signal until a predetermined condition is satisfied, such as an authorization signal, e.g., parameter data, from the remote system.

The communications device preferably comprises the at least one processor that processes the parameter data and generates the compensation factor.

In a presently preferred embodiment, the measurement device associates at least one of a fluid sample collection protocol, a sensing protocol and a processing protocol with the measurement signal, and the communications device transmits the at least one fluid sample collection protocol, sensing protocol and processing protocol to the remote system. In another, the remote system processes the at least one breath collection protocol, sensing protocol and processing protocol, generates a response signal in response to the at least one breath collection protocol, sensing protocol and processing protocol, and transmits the response signal to the communications device, and the communications device transmits the response signal to the measurement device. In such embodiment, the measurement device may adjust an operating parameter in response to the response signal, and the communications device may transmit at least a portion of the parameter data.

In accordance with another aspect of the invention, a method is provided for measuring a ketone in a fluid of a user, wherein the method comprises using a portable measurement device to measure the ketone at a first location and to generate a measurement signal indicative of the concentration of the ketone in the fluid. The method also comprises communicating the measurement signal from the measurement device to a communications device located at the first location, communicating the measurement signal from the communications device to a remote system disposed at a second location remote from the first location, and using at least one of the measurement device, the communications device and the remote system to process parameter data and generate a compensation factor for effecting a modification of the measurement signal to compensate for a compensation variable.

The measurement device may comprise a blood ketone measurement device, a urine ketone measurement device, a breath ketone measurement device, or combinations of these.

The communications device may comprise a wireless telecommunications device, a cellular phone, a smart phone such as a general purpose smart phone, and the like. The communications device preferably at least one processor and a software application, wherein the software application receives the measurement signal from the measurement device and uses the at least one processor to process the parameter data to obtain the compensation factor.

The remote system preferably is located at a remote facility, the latter of which may comprise a health care facility, a health care monitoring facility, and the like.

The parameter data may comprises any of the forms and classes noted herein above.

In a presently preferred implementation of the method, the using of the at least one of the measurement device, the communications device and the remote system to process parameter data and generate the compensation factor for effecting a modification of the measurement signal to compensate for the compensation variable comprises using the remote system to process parameter data and generate the compensation factor.

The method may further comprises pre-storing at least one of measurement device data and measurement data in the measurement device, and communicating from the measurement device to the communications device the at least one of measurement device data and measurement data in connection with the communicating of the measurement signal from the measurement device to the communications device.

The method also may further comprises communicating from the communications device to the remote system the at least one of measurement device data and measurement data in connection with the communicating of the measurement signal from the communications device to the remote system.

The using of the at least one of the measurement device, the communications device and the remote system to process parameter data and generate a compensation factor for effecting a modification of the measurement signal to compensate for a compensation variable may comprise using the remote system to process the at least one of the measurement device data and the measurement data to generate the compensation factor, and modifying the measurement signal using the compensation factor, and the method may further comprise communicating the modified measurement signal to the communications device.

The method also may further comprise communicating a portion of the parameter data from the communications device to the remote system, and the using of the at least one of the measurement device, the communications device and the remote system to process parameter data and generate a compensation factor for effecting a modification of the measurement signal to compensate for a compensation variable may comprise using the remote system to process the portion of the parameter data to generate the compensation factor.

The using of the at least one of the measurement device, the communications device and the remote system to process parameter data and generate the compensation factor for effecting a modification of the measurement signal to compensate for the compensation variable also may comprise using the communications device to process parameter data and generate the compensation factor.

The method also may further comprise using the communications device to apply the compensation factor to the measurement signal to obtain a modified measurement signal and outputting the modified measurement signal.

The method still further may comprise communicating from the measurement device to the communications device at least one of measurement device data and measurement data in connection with the communicating of the measurement signal from the measurement device to the communications device, and the using of the communications device to process parameter data and generate the compensation factor may comprise using the communications device to process the at least one of measurement device data and measurement data to generate the compensation factor using the at least one of the measurement device data and the measurement data.

The method also may further comprise communicating a portion of the parameter data from the remote system to the communications device, and the using of the at least one of the measurement device, the communications device and the remote system to process parameter data and generate a compensation factor for effecting a modification of the measurement signal to compensate for a compensation variable may comprise using the communications device to process the portion of the parameter data to generate the compensation factor.

The use of the communications device to transmit the measurement signal to the remote system preferably comprises automatically transmitting the measurement signal to the remote system upon receiving the measurement signal from the measurement device, and further preferably comprises withholding the transmission of the measurement signal to the remote signal until a predetermined condition is satisfied. The predetermined condition may comprise an authorization signal from the remote system, which in turn may comprise parameter data. The communications device preferably comprises the at least one processor that processes the parameter data and generates the compensation factor.

In a presently preferred implementation of the method, the measurement device associates at least one of a fluid sample collection protocol, a sensing protocol and a processing protocol with the measurement signal, and the communications device transmits the at least one fluid sample collection protocol, sensing protocol and processing protocol to the remote system.

The remote system preferably processes the at least one breath collection protocol, sensing protocol and processing protocol, generates a response signal in response to the at least one breath collection protocol, sensing protocol and processing protocol, and transmits the response signal to the communications device, and the communications device transmits the response signal to the measurement device.

The measurement device optionally may adjust an operating parameter in response to the response signal. The communications device also may transmit at least a portion of the parameter data. In accordance with another aspect of the invention, a method is provided for measuring a ketone in a fluid of a user. The method comprises establishing a baseline of ketone measurements for the user, selecting a measurement protocol, selecting at least one compensation variable to be addressed, providing at least one of parameter data and population data for the compensation variable, measuring the ketone in the fluid to obtain a measurement signal, using the measurement signal and the at least one of parameter data and population data to obtain a compensation factor, and using the compensation factor to effect a modification of the measurement signal. The baseline may comprise a normal state, but need not.

The method may further comprise pre-storing the at least one of the parameter data and the population data. The using of the compensation factor to effect the modification of the measurement signal may comprise applying the compensation factor to modify a level of the measurement signal. The using of the compensation factor to effect the modification of the measurement signal may comprise identifying the compensation factor to the user. It also may comprise displaying the compensation factor to the user, plotting the compensation factor in an output, transmitting the compensation factor as an output, and the like.

In accordance with still another aspect of the invention, an apparatus is provided for sensing an analyte in breath, wherein the apparatus comprises (a) a breath input that inputs the breath and directs it to a breath sensor according to a breath collection protocol, (b) a breath sensor that quantifies the analyte in breath and generates a signal, wherein the breath sensor is pneumatically coupled to the breath input, and operates according to a sensing protocol, (c) a processor that is operatively coupled to the breath sensor and operates according to a processing protocol, wherein the processor uses computerized functions to improve the correlation between the signal and the underlying physiology, and (d) wherein the processor is configured to alter the breath collection protocol, the sensing protocol and the processing protocol based on input provided to the apparatus to provide clinically enhanced information about the breath analyte to the user.

The input provided to the apparatus may be based on one of (i) a test purpose as input by a user and (ii) a remote system. It also may be generated by historical information amassed by the controller.

The breath collection protocol may comprise any of: (i) rebreathing, (ii) non-rebreathing, (iii) discarding, (iv) segmenting, (v) single exhalation, (vi) resting state, (vii) hyperventilation, and (viii) heart rate compensation.

The sensing protocol may comprise at least one of a sensor protocol, a flow control protocol, a heating protocol, and a subtraction protocol.

The data processor may rely on information obtained from a supplementary sensor. The supplementary sensor may comprise one of a heart rate monitor and a glucose meter.

The remote system may obtain information from a plurality of breath analyzers.

The breath sensor in some embodiments does not operate using chromatography principles.

In accordance with yet another aspect of the invention, an apparatus is provided for sensing at least two analytes in breath. The apparatus comprises (a) a breath input that accepts a first analyte and a second analyte, (b) an analyzer that senses the first analyte to generate a first signal and, independent from the generation of the first signal, senses the second analyte to generate a second signal, (c) a transmission device that is operatively coupled to the analyzer that transmits the second signal to a remote system, and (d) a processor that is operatively coupled to the analyzer that reports the first signal, and not the second signal, to a user, but only if the transmission device reports a successful transmittal of the second signal to the remote system. The first analyte is related to a physiological process that is well characterized and the second analyte is related to a physiological process that is less understood.

The remote system may assess the second signal in the context of the first signal and, if appropriate, causes the processor to display the second signal.

In accordance with yet another aspect of the invention, a method is provided for measuring an analyte in breath of a user using a breath analysis device comprising a sensor. The method comprises providing normal state information to the breath analysis device indicative of a normal state of the user, inputting the breath into the breath analysis device and exposing the breath to the sensor to obtain an analyte measurement, inputting a measurement state of the user indicative of a state of the user when the user provided the breath for input into the breath analysis device, using the breath analysis device to process the measurement state and the normal state to generate a compensation factor, and using the compensation factor to adjust the analyte measurement.

The normal state information may comprise a normal heart rate of the user, and the measurement state information comprises a heart rate of the user when the breath is inputted into the breath analysis device.

The normal state information may comprise a normal blood pH of the user, and the measurement state information comprises a blood pH of the user when the breath is inputted into the breath analysis device. The normal state information also may comprise a normal barrier to transport in the lungs of the user, and the measurement state information may comprise a barrier to transport in the lungs of the user when the breath is inputted into the breath analysis device. The normal state information also may comprise a normal alveolar wall thickness of the user, and the measurement state information comprises an alveolar wall thickness of the user when the breath is inputted into the breath analysis device. The normal state information further may comprise a normal activity level of the user, and the measurement state information comprises an activity level of the user when the breath is inputted into the breath analysis device. The normal state information also may comprise a normal external temperature of the user, and the measurement state information comprises an external temperature of the user when the breath is inputted into the breath analysis device. The normal state information also may comprise a normal energy use of the user, and the measurement state information comprises an energy use of the user when the breath is inputted into the breath analysis device. The normal state information still further may comprise a normal menstrual condition of the user, and the measurement state information comprises a menstrual condition of the user when the breath is inputted into the breath analysis device.

According to still another aspect of the invention, a method is provided for measuring an analyte in breath of a user using a breath analysis device comprising a sensor. The method comprises providing normal state information to the breath analysis device indicative of a normal state of a user population, inputting the breath into the breath analysis device and exposing the breath to the sensor to obtain an analyte measurement, inputting a measurement state of the user indicative of a state of the user when the breath is inputted into the breath analysis device, using the breath analysis device to compare the measurement state with the normal state to generate a compensation factor, and using the compensation factor to adjust the analyte measurement.

The normal state information may comprise a normal heart rate of the user population, and the measurement state information comprises a heart rate of the user when the breath is inputted into the breath analysis device. The normal state information also may comprise a normal blood pH of the user population, and the measurement state information may comprise a blood pH of the user when the breath is inputted into the breath analysis device. The normal state information also may comprise a normal barrier to transport in the lungs of the user population, and the measurement state information comprises a barrier to transport in the lungs of the user when the breath is inputted into the breath analysis device. The normal state information also may comprise a normal alveolar wall thickness of the user population, and the measurement state information comprises an alveolar wall thickness of the user when the breath is inputted into the breath analysis device. The normal state information further may comprise a normal activity level of the user population, and the measurement state information comprises an activity level of the user when the breath is inputted into the breath analysis device. The normal state information also may comprise a normal external temperature of the user population, and the measurement state information comprises an external temperature of the user when the breath is inputted into the breath analysis device. The normal state information also may comprise a normal energy use level of the user population, and the measurement state information comprises an energy use level of the user when the breath is inputted into the breath analysis device. The normal state information similarly may comprise a normal menstrual condition of the user population, and the measurement state information comprises a menstrual condition of the user when the breath is inputted into the breath analysis device.

In accordance with another aspect of the invention, a method is provided for measuring a ketone in a fluid of a user. The method comprises using a portable measurement device to measure the ketone at a first location and to generate a measurement signal indicative of the concentration of the ketone in the fluid, automatically communicating the measurement signal from the measurement device to a communications device located at the first location, and automatically communicating the measurement signal from the communications device to a remote system disposed at a second location remote from the first location.

In accordance with another aspect of the invention, a method is provided for measuring a ketone in a fluid of a use. The method comprises, in a first phase, using a portable measurement device to measure the ketone at a first location and to generate a measurement signal indicative of the concentration of the ketone in the fluid, communicating the measurement signal from the measurement device to a communications device located at the first location, and communicating the measurement signal from the communications device to a remote system disposed at a second location remote from the first location. During the first phase the measurement signal is withheld from the user. The method also comprises, in a second phase performed after completion of the first phase, selectively communicating an authorization from the remote system to the communications device, and upon receipt of the authorization by the communications device, outputting the measurement signal to the user using at least one of the measurement device and the communications device.

The communicating of the measurement signal from the measurement device to the communications device and the communicating of the measurement signal from the communications device to a remote system preferably are automatic.

BRIEF DESCRIPTION OF DRAWINGS

The accompanying drawings, which are incorporated in and constitute a part of the specification, illustrate a presently preferred embodiments and methods of the invention and, together with the general description given above and the detailed description of the preferred embodiments and methods given below, serve to explain the principles of the invention. Of the drawings:

FIG. 3 is a process flow diagram illustrating a process for measuring one or more ketones in the one or more body fluids according to a preferred implementation of another aspect of the invention;

DETAILED DESCRIPTION OF THE PREFERRED EMBODIMENTS AND METHODS OF THE INVENTION

Figure 1:
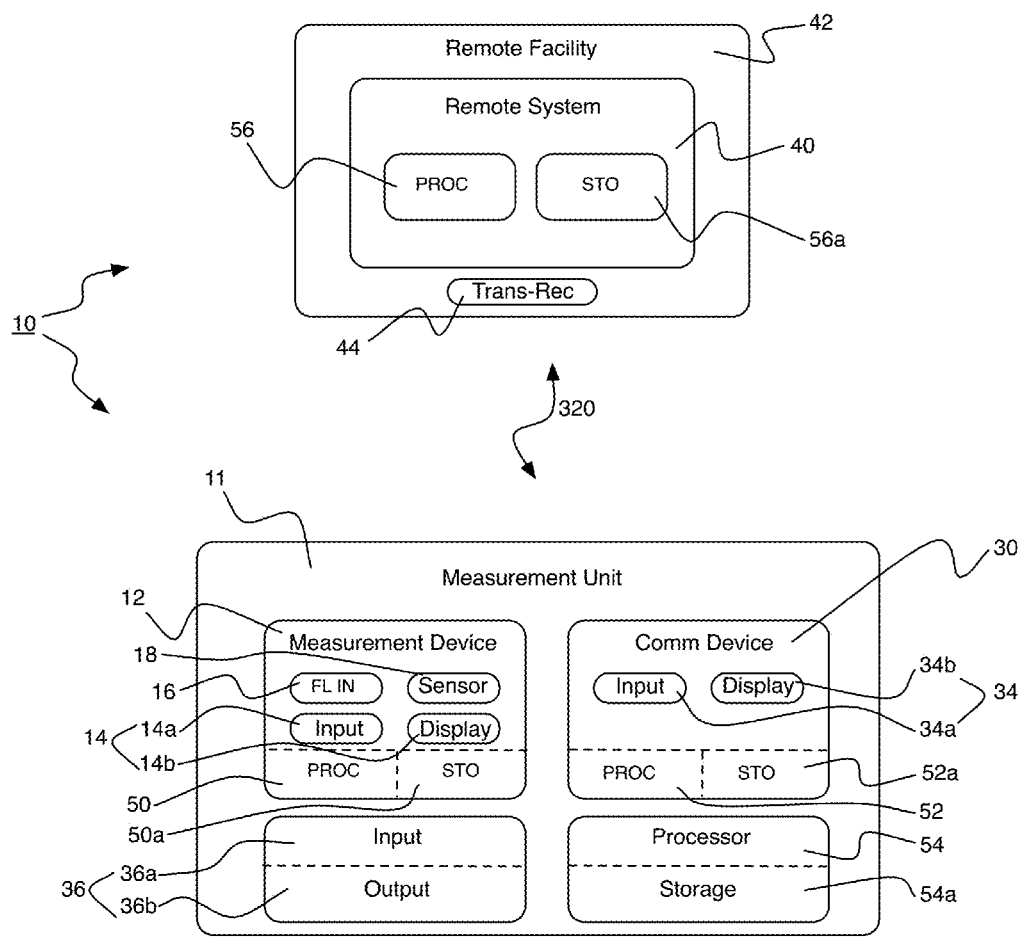
FIG. 1 shows a system for measuring one or more ketones in one or more bodily fluids in accordance with a presently preferred embodiment of one aspect of the invention, wherein the ketone measurement device and the communications device are integrated into a measurement unit.

Reference will now be made in detail to the presently preferred embodiments and methods of the invention as described herein below and as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the preferred embodiments and methods. The invention according to its various aspects is particularly pointed out and distinctly claimed in the attached claims read in view of this specification, and appropriate equivalents.

With reference to FIG. 1, a system 10 is provided for measuring a ketone in a fluid of a user. System 10, which represents a presently preferred embodiment of the invention, is designed to measure the concentration of one or more ketones in one or more body fluids, most notably blood, urine, breath, or some combination of these, at ketone concentrations normally encountered in those respective fluids under circumstances for which the measurement is intended to address. For measurements in healthy users, for example, the ketone measurement is within the range of normal ketone levels for healthy users and, for measurements of users with a particular condition, e.g., obesity, diabetes, metabolic syndrome, etc., the measurement is within ranges expected to be encountered under those circumstances.

System 10 comprises a portable integrated measurement unit 11 that in use would be in the possession of or co-located with a user at a first location.

Measurement unit 11 (including the associated communications device described herein below) is designed to be used and operated by a "user" (e.g., a dieting person, athlete, patient, etc.) whose ketone concentrations are being measured. It is amenable to use by the user alone, for example, without the presence or assistance of a friend, aid, nurse or clinical staff, etc. Measurement unit 11 also is amenable, however, to use by a person other than the "user" whose ketones are being measured, for example, such as a coach, trainer, doctor, nurse, clinical technician, family member, friend and the like. Thus, although the "user" is the person whose ketone levels are being measured, the "user" may or may not also be the person who performs the manual commands and operations using unit 11. For simplicity and ease of illustration, throughout the detailed description section in this document, the "user" is assumed to be both the person whose ketones are measured and the operator of the measurement unit, even though this may not be and need not be the case in a given instance or application of the system, unless indicated otherwise.

Measurement unit 11 also is designed, sized and configured to be used not only in a clinical setting, (e.g., in a hospital, out-patient clinic, physician's office, nutritionist's office, diet treatment center, laboratory, and so on), but also in non-clinical settings, (e.g., the user's home, office, workplace, gym, while traveling, and so on). It is portable in that it is sufficiently small and light weight that it can be conveniently lifted and carried and used by an individual at various locations. Although hand-held devices are included, this portability also includes table-top configurations and the like, provided they can be lifted, moved and carried by an individual.

The "first location" as the term is used herein preferably comprises a location at which a user of the system, such as the user whose ketone levels are being measured, is located. Given the fact that the user-based unit 11 is portable, it typically would be located with the user, or at a location that is readily available to the user, such as the user's home or workplace. Unit 11 could, however, be kept in the user's or user's vehicle, purse, backpack, and the like. This first location also could comprise a treatment facility, such as a treating physician's office, hospital, outpatient clinic, and the like.

Unit 11 comprises a ketone measurement device 12 that measures the concentration of the ketone or ketones of interest within the fluid or fluids of interest. Fluids of interest with respect to system 10 include blood, urine and breath. Ketones of interest with respect to system 10 depend upon the fluid being measured. The term "ketone" is being used broadly to refer to the three endogenously produced ketone bodies: acetone, acetoacetic acid, and β-hydroxybutyric acid ("β-HBA"), and their conversion equivalents. This term applies regardless of whether the molecule is technically a ketone or whether, for example, it is resonantly equivalent to another class of molecule. For instance, β-hydroxybutyric acid (β-HBA), is technically a carboxylic acid rather than a ketone but is nonetheless commonly referred to in the field as a blood ketone. For blood-based measurements, the ketones of interest typically include acetoacetate, β-HBA or β-hydroxybutyrate ("β-HB"), and in some cases acetone. (Note that, as is customary in the ketone measurement field, reference herein to β-HB also may comprise β-HBA, and the converse.) Ketones in urine include primarily acetoacetate. The primary ketones of interest in breath is acetone.

Measurement device 12 is indicated generally in FIG. 1 based on its common function as a device for measuring ketones, but typically will comprise a different device or design for each of the three fluids of interest. Separate embodiments for each of the three fluid applications are shown in the drawings and described herein below. This is not necessarily limiting, however, in that measurement devices that combine or incorporate multiple fluid measurement capacities or modalities can be configured. An example would be a measurement device in which a combination of the blood, urine and/or breath measurement devices disclosed herein below are integrated into a single housing.

Figure 17:
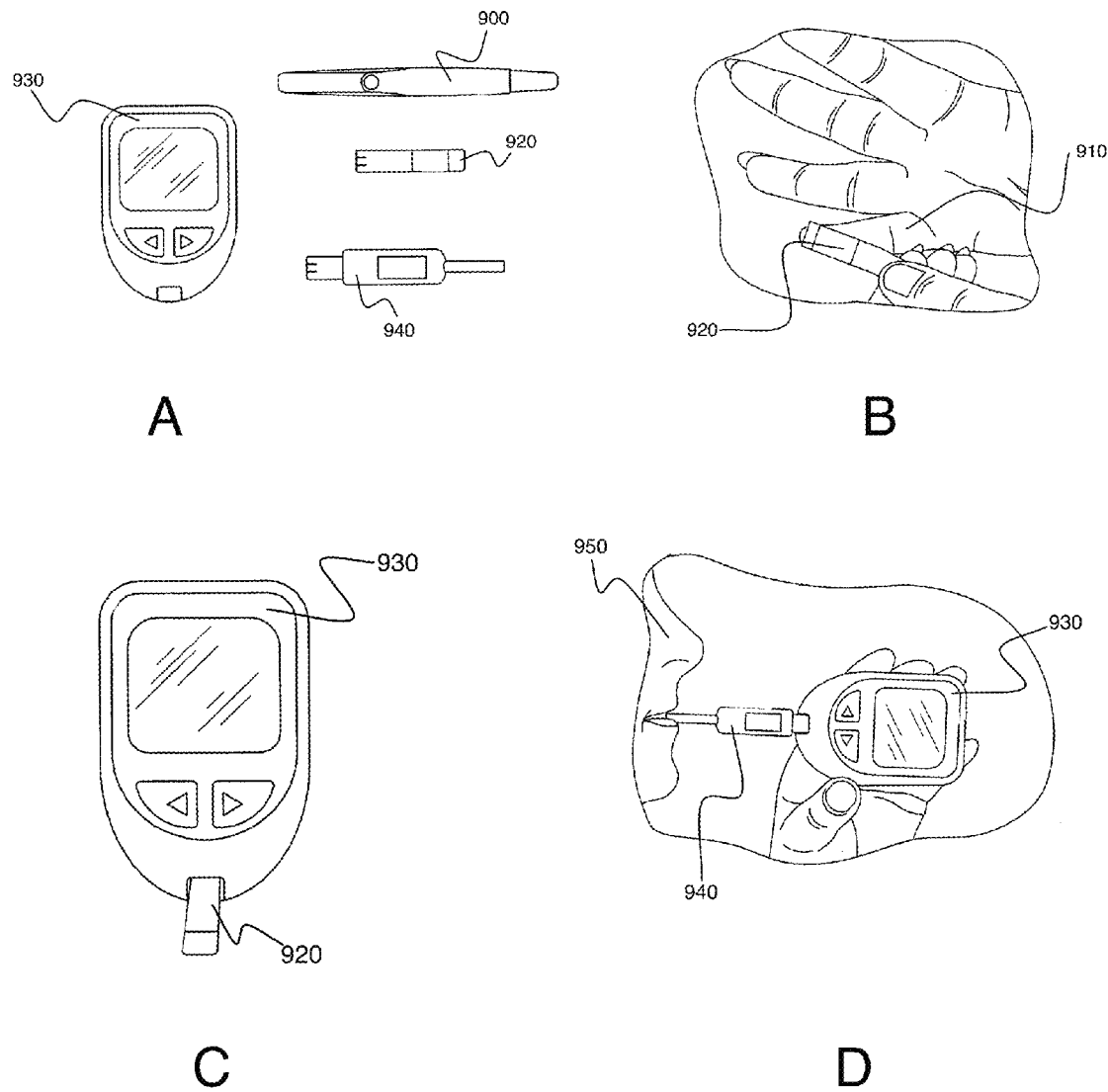

An example of an integrated device is shown in FIG. 17. Here, the user 950 uses a lancet 900 to prick his or her finger 910 to obtain a drop of blood. The blood is deposited to a test strip 920, which is inserted into a meter 930. The same meter can be coupled to a mouthpiece 940, which the user 950 can exhale through as shown in FIG. 17D.

In each of the aforementioned measurement devices, the device receives a sample of the fluid or fluids and measures ketone analyte or analytes in the fluid or fluids to ascertain the presence and preferably the concentration or concentration range of the ketone or ketones of interest in the fluid or fluids. The term "measure" or, equivalently, "sense," as used herein may comprise analysis to ascertain or detect a specific concentration of the analyte in the fluid, or to detect the presence of the analyte above a specified threshold concentration, or to detect whether the concentration of the analyte is within a particular range or ranges, and the like.

Measurement device 12 optionally may comprise an input device 14a for inputting data or information into measurement device 12. Input device 14a may comprise a keyboard, mouse, tracking device, or other device capable of inputting data and information as further described herein. Measurement device 12 also optionally may comprise an output device 14b, e.g., such as a display, for presenting user information and outputting measurement results. Preferably, input device 14a and output device 14b of measurement device 12 are integrated in the form of a touch screen display 14.

Measurement device 12 also comprises a fluid sample input 16 and a sensing system 18. Fluid sample input 16 is designed to receive a sample of the fluid to be analyzed. It typically will differ in design depending on the specific fluid.

Sensor system 18 is designed to analyze the fluid and measure the concentration of the ketone or ketones of interest in the fluid, and to generate a measurement signal that is representative or indicative of the measurement result, i.e., here the ketone concentration in the fluid. Appropriate sensor systems include, without limitation, colorimetric sensors, enzymatic and electrochemical sensors, thermal and thermoelectric sensors such as thermopile sensors, nanoparticle or metal oxide-based sensors, and so on. Examples of colorimetric sensors are provided in U.S. Provisional No. 61/800,081, commonly assigned to the assignee hereof and are hereby incorporated herein by reference as if fully set forth herein. Examples of metal oxide or nanoparticle sensors are provided in U.S. application Ser. No. 13/052,963, commonly assigned to the assignee hereof and are hereby incorporated by reference as if fully set forth herein. Other examples of sensors are provided in U.S. Pat. Nos. 6,609,068 and 7,364,551, commonly assigned to the assignee hereof and are hereby incorporated by reference as if fully set forth herein.

Unit 11 also comprises a communications device 30. Communications device 30 is in operative communication with measurement device 12 and is adapted or configured to receive the measurement signal from measurement device 12, or from an associated processor or processing means (described more fully herein below).

Measurement device 12 and communications device 30 are in operative communication in the sense that they are configured to communicate information in the form of digital data at least from one device to the other and preferably bi-directionally between the two devices, directly or indirectly, e.g., such as via an intermediate processor. This operative communication may be enabled through a direct connector (such as printed circuit board connector or slot), a docking station, a cable, or wirelessly, as further described herein below. In unit 11, the communication between these devices is via a direct connection, e.g., by being affixed on a common circuit board or adjacent circuit boards with ohmic connection, via a cable, or the like.

Communications device 30 also comprises a capability to transmit the measurement signal, in its raw form or in modified form as further described herein, outwardly from unit 11. Preferably, this outward or external communications capability comprises data receiving capabilities so that communications device 30 can transmit and receive data bi-directionally, both to and from unit 11. Presently preferred embodiments of this outward or external communications feature of communications device 30 comprise a data modem, a wireless transceiver, or combinations of these. Presently preferred examples of suitable wireless technology include the transmission circuitry and associated software of commercially-available cell phones or "smart phones," Bluetooth transceiver technology, and the like. Alternatively or in addition, however, the communication may comprise a wired connection, e.g., to the Internet.

Communications device 30 optionally also may comprise an input device 34a such as a keyboard, keypad, mouse, track ball, and the like, for inputting information or data, and a display 34b, e.g., for displaying user information, data, and measurement results. Presently preferred input and display devices may comprise or be combined or associated with or as a touch screen 34.

In system 10, unit 11 comprises both measurement device 12 and communications device 30, and thus, it is generally preferred that a single input device 36a and a single display 36b are used for both device 12 and device 30. This obviates the need to provide separate input and display devices for each of them, thereby potentially lowering size, weight, complexity and unit cost. More preferably, and as in unit 11, input device 36a and display 36b are combined in the form of a touch screen 36 that serves both devices 12 and 30.

Unit 11 also optionally may comprise a clock, calendar, and a locating device such as a Global Positioning Satellite (GPS) receiver.

System 10 further comprises a remote system 40 disposed at or within a remote facility 42 (also referred to herein as a "center facility 42") at a second location remote from the first location. The distance between the first and second locations may be substantial, e.g., in separate cities, states, provinces, regions, etc. This is not, however, necessarily the case. In a clinical setting, for example, the first location where unit 11 is located may be in an examination room and remote system 40 may be in a separate room in the same facility.

Remote system 40 may comprise any computer, or system or network of computers, that processes, stores and/or communicates information remotely from any of unit 11, measurement device 12 or communications device 30, as generally described herein. Remote system 40 preferably comprises a general purpose or commercially-available server with appropriate server software and preferably known or commercially-available database software capable of performing the tasks and functions as described herein. Remote system 40 may transmit current information, previous information, information that has been acquired subsequent to the measurement or data of interest, or combinations of these.

Remote system 40 also comprises a transceiver device 44 suitable and appropriate for communications, preferably bi-directional or duplex communications, with communications device 30 of unit 11. Transceiver 44 may comprise any of the technologies described herein above with respect to communications device 30.

Remote facility 42 may comprise a data center, health care facility such as a hospital, clinic, or doctor's office, and the like. The location of remote system 40 and remote facility 42, however, need not be fixed, and remote system 40 may be moved to a new location or locations, e.g., from time to time. Remote system 40 also may comprise a distributed network. In presently preferred system designs, remote facility 42 comprises a data center that comprises one or more servers (remote system 40) for storing, managing and inputting and outputting or distributing data as described more fully herein below. This is not, however, limiting. Remote facility 42 may, for example, comprise a set of regional facilities, a distributed data management system with multiple facilities, and the like. Additionally, remote system 40 may either be under the operational control of the user of the system (e.g., system 10), or it may be under the control of a third-party, e.g., a service provider.

In presently preferred embodiments, remote facility 42 comprises an Internet service or cloud provider that services various customers, and which serves as a portal or repository for the facilities that also may comprise part of the remote facility 42, e.g., such as a hospital, clinic, doctor's office, and the like.

Remote system 40 comprises a database, for example, such as any one of the several commercially-available database application systems that is configured to store and transmit or receive data as described herein. An example would comprise the types of commercially-available databases that are used to house and manage health records.

With this system 10 as herein described, communications device 30 of unit 11 and remote system 40 are configured to communicate data, preferably but optionally bi-directionally, preferably including the measurement signal and additionally parameter data and population data as described more fully herein below. This communications link, indicated by reference numeral 32, preferably is at least partially wireless and preferably includes an Internet connection or access.

Measurement device 12 and communications device 30 each require a certain amount of processing power or capability to perform their respective functions. Accordingly, measurement device 12 preferably comprises a processor 50 and communications device 30 preferably comprises a processor 52. Measurement device 12 and communications device 30 also preferably comprise storage to store data useful in their operations and to support the operations of their respective processors. Accordingly, measurement device 12 preferably comprises storage 50a and communications device 30 preferably comprises storage 52a. More preferably in integrated unit 11, processors 50 and 52 comprise a single or combined processor 54 that performs processing functions required by each of its supporting devices 12 and 30, and storage devices 50a and 50b comprise a single storage device 54a that is shared by devices 12 and 30, directly or indirectly, e.g., via the unified processor.

Consistently with the description herein above, remote system 40 comprises a processor 56 and associated storage 56a.

In each of these references to storage, the storage medium, device or capability preferably comprises known or commercially-available forms of digital data storage, for example, such as random access memory, a mass storage device such as a hard drive or flash memory device, a removable storage medium, and the like.

In system 10, measurement device 12 and communications device 30 are contained within a single unit (unit 11) and comprise functionally or operationally integrated devices. This configuration, however, is not limiting. The measurement device and the communications device, for example, may be physically separate from one another and operative as separate devices.

Figure 2:
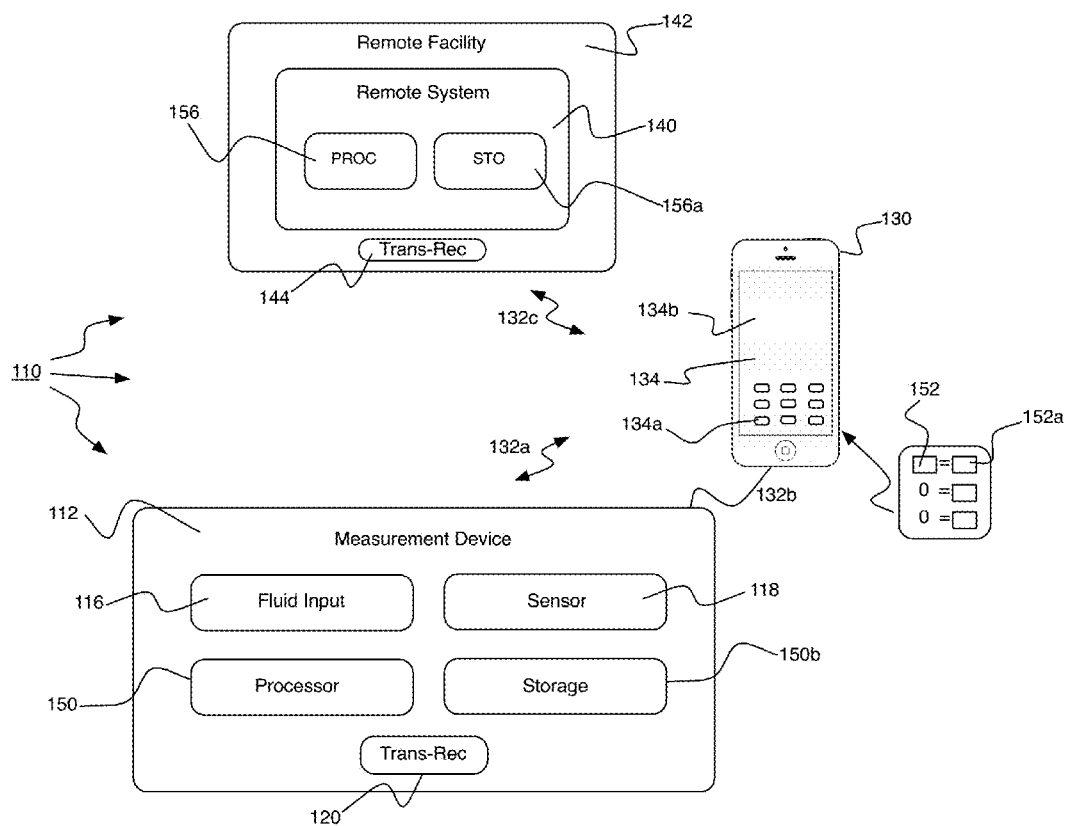
FIG. 2 shows another system for measuring one or more ketones in one or more bodily fluids in accordance with a presently preferred embodiment of one aspect of the invention, wherein the measurement device and the communications device are physically separated components.

FIG. 2, for example, illustrates a system 110 that comprises a portable measurement device 112 functionally equivalent to measurement device 12 of system 10, and a portable communications device 130 functionally at least equivalent to communications device 30 of system 10, but wherein measurement device 112 and communications device 130 are separately contained units, albeit in operative communication with one another, as represented, for example, by wireless communications link 132a.

Measurement device 112 may comprise any of a range of portable ketone measurement devices for measuring the concentration of one or more ketones in one or more body fluids, as described herein above with respect to measurement device 12. Measurement device 112 comprises a fluid sample input 116, a sensing system 118, a processor 150 and associated storage 150a, each as described herein above with respect to measurement device 12.

Measurement device 112 further comprises a measurement device transceiver subsystem 120 that is operatively coupled with and under the control of processor 150, and is configured to communicate, preferably bi-directionally with communications device 130. Transceiver subsystem 120 may comprise any one or combination of a number of known or commercially-available communications technologies or subsystems, e.g., including a modem, a wireless connection, etc.

Although communications device 130 may comprise essentially any device capable of meeting the minimal requirements and capable of performing the functions and tasks as described herein, in system 110 it preferably comprises a non-wired transmitting device such as a Smart Phone or a tablet. Communications device 130 preferably comprises a wireless device, more preferably a cellular telephone, and even more preferably a "smart phone" that comprises not only telephone circuitry but built-in processing capability, a clock, a calendar or date indicator, and positioning circuitry such as a GPS or similar geolocation and mapping capability.

More specifically, in the presently preferred embodiment of system 110, communications device 130 comprises a Pre-Owned Consumer Electronic Device ("POCED"). A POCED as the term is used herein is a generally-available consumer electronic device that is designed for general purposes, such as a cellular telephone, a smart phone, and the like, and that is capable of being programmed or otherwise configured with software, e.g., an application or "app," that performs the functions and tasks described herein with respect to communications device 130. Examples of POCEDs would include an Apple iPhone®, an Android® smart phone, and the like. Incidentally, notwithstanding the term "pre-owned," the device need not necessarily be previously owned by the user. Nor is it necessarily the case that the device must be strictly or even mainly for consumers. The term POCED merely means that the electronic device is or has been commercially available for uses other than as a dedicated communications device for use in system 110, and was designed either as a general purpose device or for a purpose other than as a dedicated communications device for use in system 110.

The communications device 130 is in operative communication with measurement device 112, in the sense that the devices have the ability to communicate data between them, either uni-directionally from one to the other or, more preferably, bi-directionally between them. Measurement device 112 and communications device 130 preferably communicate via a wireless communications link, but optionally or alternatively may be coupled directly or ohmically, e.g., via a detachable cable 132*b*.

Communications device 130 further comprises an input 134*a* and a display 134*b* for inputting information or data, for responding to queries or options presented to the user on display 134*b*, for presenting results, and so on. Optionally or alternatively, input 134*a* may comprise a detachable input device, such as a detachable keyboard or keypad and mouse to facilitate the input of data and information. The display also may be detachable, or device 130 may accommodate a detachable monitor as an accessory. As an alternative to input 13*a* and display 134*b*, device 130 may combine the two into a touch screen 134 that both provides displays and permits data input.

Both measurement device 112 and POCED 130 are disposed at a first location, as described herein above and, as noted herein above, are in operative communication, e.g., via wireless link 132*a*.

System 110 further comprises a remote system 140 disposed at a second location within a remote facility 142, each as previously described herein above with respect to remote system 40 and remote facility 42 of system 10.

Communications device 130 and remote system 140 are configured to communicate with one another, preferably wirelessly and more preferably via a network such as the Internet, as generally represented in FIG. 2 by wireless link 132*b*. The communications link between them preferably but optionally is bi-directional. In system 110, communications device 130 transmits the measurement signal, as received or as modified as described herein, and in some applications parameter data and/or population data (described herein below) to remote system 140. Remote system 140 similarly is configured to transmit parameter data and population data to communications device 130 and, via the latter, to measurement device 130.

The general operation of presently preferred systems 10 and 110 are very similar, particularly given the similarity in their configurations. To simplify the illustration, this general operation will be made with respect to system 110.

With reference to FIG. 2 and flow chart shown in FIG. 3, the method commences at step 1, wherein the user powers up measurement device 112 at the first location. If some preliminary setup or configuration is required with the particular measurement device and test, the user then undertakes that setup or configuration.

In the second step, the user powers up communications device or POCED 130 and calls up a software app, also at the first location. The basic functions of the software app will be described here, in conjunction with FIG. 3. Upon call up of the app on POCED 130 by the user, the app initializes the POCED, establishes or confirms a communications link with measurement device 112, and displays a "Ready" message on touch screen 134 of the POCED.

In the third step, the user prepares the fluid sample if the measurement device and method call for this. Such preparation may comprise, for example, obtaining a blood sample through a finger tip prick and placing the blood droplet from the finger tip onto a blood ketone test strip, or obtaining a urine sample and dipping a urine ketone test strip into the sample to dispose the urine sample onto the test strip. In the analysis of breath acetone, an example is provided in connection with the breath acetone analysis devices disclosed in the present assignee's U.S. Provisional Patent Application No. 61/800,081, which is incorporated herein by reference as if fully set forth herein. In it, the user prepares a breath sample, e.g., by exhaling into a breath bag to create the breath sample, and placing the inflated bag on the base of the breath analysis device.

This step also comprises inputting the fluid sample into measurement device 112, and selecting "Run Test" from touch screen 134 of device 130, which causes measurement device 112 to conduct the ketone measurement or test. This test comprises using sensing system 118 of measurement device 112 to analyze the sample and measure the concentration of the ketone or ketones in it, generating a measurement signal that is indicative or representative of this measured concentration. In this presently preferred implementation, measurement device 112 automatically transmits the measurement signal to POCED 130.

The fourth step, performed by the POCED under control of the software app upon its receipt of the measurement signal, is to automatically analyze or process the measurement signal, to modify the measurement signal as is appropriate (described more fully herein below), and to transmit the measurement signal, either in its originally-received form but with the modification information, or as modified by the POCED, to remote system 140.

The fifth step, performed by the remote system 140 upon receipt of the measurement signal, originally or as modified, is to store it in an appropriate place, preferably in a user records database, in storage 156*a*. Remote system 140 optionally may transmit a confirmation signal to the POCED, e.g., acknowledging or confirming receipt of the measurement signal. Remote system 140 also optionally may further analyze or process the measurement signal.

In a given application, it is possible that less than all of these steps may be applied, that tasks within the steps as described here may vary or differ, that additional steps or tasks may be employed, and the like. The processing described here and outlined in FIG. 3, however, provides a basic or general method implementation that will serve to illustrate the multiple variations that are described herein below, and which are embodied by the invention as set forth in the appended claims.

Variables in Ketone Measurement

Physiological and pathophysiological processes that are responsible for the presence of ketones in body fluids to a certain extent are known, although some are not well understood, some are based at this point on theory more than clinical or laboratory-based evidence, and it is reasonable to assume some are as yet unknown. In making ketone measurements using essentially any practical ketone measurement system, there are a host of factors or variables that can affect the result.

Ketones are known to be correlated with fat metabolism, which is relevant in a number of user-related circumstances. One is in managing a weight loss or weight gain program or regiment. In a weight loss program, an indication of fat loss as indicated by the presence of elevated ketone levels indicates that the program is effective in reducing fat and thus weight. Ketone measurements also can be an effective indicator of user compliance with the program.

Ketones are produced in the body as a result of lipid metabolism. Increased lipid metabolism is seen in two common situations. In health management, individuals may elect to consume a low carbohydrate diet. When the body is in a low carbohydrate state, it preferentially metabolizes fat. Such a state is associated with reduced insulin levels, which has various health benefits, including sometimes promoting weight loss and decreasing blood pressure. For individuals with diabetes, living a low carbohydrate lifestyle may allow those individuals to reduce their medication dosage or eliminate certain medications.

For certain diabetics, most commonly Type 1 diabetics, if the body has insufficient sugar, it resorts to metabolizing fat. This increase in fat metabolism results in increased ketone production. Ketones are acidic and, therefore, a build-up of ketones can cause a shift in blood pH, assuming that the body's ability to buffer pH is compromised. This can result in a condition called diabetic ketoacidosis.

To illustrate the vulnerability of ketone measurement to variations, consider the physiological and related processes responsible for causing a particular analyte to be present in a body fluid sample. Such processes usually vary from analyte to analyte and almost invariably are multi-step in nature. Typically, however, they involve generation of the analyte or some form of precursor of it at some location in the body, e.g., within a particular line of cells, in a particular organ, etc. The analyte or precursor then enters the bloodstream, e.g., via capillary beds, where it travels through the vascular system. Although the local ketone composition of the blood may change depending, for example, on the specific anatomical location from which the blood sample is drawn, a blood sample may be obtained in known fashion through a number of means, including fingertip puncture, hypodermic withdrawal, etc.

Again, depending on the analyte or precursor, as the blood enters the renal system, some portion of the analyte or precursor may be filtered in the kidneys and be incorporated into the urine. Samples typically are obtained by collecting a urine sample from the user upon the occurrence of a routine urination, as is known in clinical settings.

As the blood enters and passes through the cardio-pulmonary system, gas-phase analytes or precursors in the blood diffuse through the alveolar-capillary or respiratory membrane and into the spaces in the alveolar sacs. From there, it or they diffuse in and through the lungs, through the bronchial areas and upper airways and are exhaled in the breath.

At each stage, the analyte or precursor is vulnerable to re-absorption or adsorption, chemical reaction or interaction with other fluids or materials, etc.

Ideally, the measurement of the analyte or analytes of interest as obtained from the fluid will be highly correlated with and accurately reflect the concentration of the analyte or precursor at its anatomical site of generation, and therefore ideally will be a true reflection of the physiological or pathophysiological event that is being monitored or diagnosed through the ketone analysis. Given the multiple steps and phenomenology, even in this physiologically-focused analysis, one can see that there is a myriad of variables or factors that can cause the true or ideal correlation between analyte or precursor generation and measured analyte concentration in the fluid sample to be impaired or lost.

Even where one or more variables or factors are known and are taken into consideration, this rarely if ever has occurred during the measurement process or contemporaneously with it. Typically, if such variables are even considered, they are part of pre-planning for a controlled clinical study, or as a post-measurement consideration. Far more typically, data necessary to identify or quantify the phenomena that caused the correlations to be impaired or obscured were not obtained at the time of testing, they cannot be obtained after the fact, and therefore they are unavailable.

Parameter Data and Compensation

Systems and methods according to aspects of the invention successfully address this variability by generating and applying one or more "compensation factors" that compensate for the actual or anticipated effects of variables associated with various aspects of the ketone measurement. As part of such systems and methods, one or more variables of interest or "compensation variables" are identified, their actual or anticipated effects on the ketone measurement are ascertained, one or more corresponding compensation factors are generated or selected, and the one or more compensation factors are used to modify, adjust or annotate the ketone measurement to offset, nullify or otherwise address or accommodate the variable or variables.

Each of the variables that is considered or addressed in a given application by definition has or is capable of having some variation. Where this variation is quantified or quantifiable, some form of units typically can be used to express the value or values of the variable. Where the variable of interest is the age of the user, for example, that age can be expressed in years, or, in pediatric applications, months. Correspondingly, compensation factors for such quantitative variables similarly can be expressed in those same quantitative units. As an hypothetical example, in a given case it may be established empirically that users in the age range of 5-10 years on average have 20% less acetone on a concentration basis in the exhaled breath as users in the 20-30 year age range. Accordingly, when taking ketone measurements for a 5 year old user, the system would multiply the ketone concentration of the 5-year old user by a compensation factor of 1.25 (=1/0.8) to make normalized comparisons with ketone measurements of users in the 20 to 30 year old range.

These values of respective variables of interest in ketone measurements are referred to herein as "parameter data."

Some variables are more qualitative and do not lend themselves well to quantitative characterization. The state or condition of the variable relative to the ketone measurement, however, nonetheless may have an impact on the measurement result. Instead of a quantitative variable such as the age of the user, for example, the variable may assume only a limited number of states, for example, male or female, pathology present or not present, stress level low, intermediate or high, and so on. Thus, although the state of the variable itself may not be conveniently represented quantitatively, it may have an impact on the ketone measurement result that can be quantified. The level or condition of such qualitative variables may be referred to herein as "parameter information." For simplicity of description and illustration herein, and because often such variables can be treated similarly or identically, the term "parameter data" as it is used herein includes both quantitative parameter data and qualitative parameter information, unless indicated otherwise.

In some preferred embodiments and method implementations according to aspects of the invention, it is desirable to establish an initial reference point, condition or set of conditions, against which actual ketone measurement results can be compared to identify or evaluate changes, e.g., over time. This initial reference point, condition or set of conditions may comprise or reflect a "baseline," e.g., a normal state, an expected value or set of values, a selected starting point, or the like, from which ketone measurements according to various aspects of the invention may be measured or compared. The "baseline" in general terms is a standard or reference value or set of values for a factor relevant to analyte measurement (including the measurement of multiple analytes), that is expected to change for a given user from time to time or measurement to measure, or for a given user relative to a population of users (e.g., from a statistical norm). If a user is about to commence a new weight loss program, for example, the user's ketone levels for a period of time immediately prior to commencing the program may serve as a baseline. As the program is undertaken and progresses, ketone measurement results can then be compared to the baseline to better understand the subsequent ketone measurement results and thus to better evaluate the effectiveness of the program, the user's compliance with the program, and the like. In another example, this one involving evaluation of a drug regiment, if one were to measure the concentration of a particular analyte before and after administration of a drug, for example, the baseline generally would be the analyte concentration before the drug were administered. If one were to measure analyte concentration as part of monitoring a physician-prescribed diet, the "baseline" generally would be the analyte concentration just before the diet began.

A baseline in a general sense of the term merely represents a logically- or arbitrarily-designated starting point from which to judge or evaluate other measurement results, usually subsequent to the baseline. An example of a particular baseline, and often a relatively useful and potentially important one, involves a "normal state" of the user. Although the "normal state" of the user typically is a relative term or factor that can depend on various factors as well the specific analyte being measured, it is generally understood to reflect a long term desired state of health and wellness. A "normal" weight for a user, for example, might be a weight that is suitable, appropriate or even ideal for a person of the user's height and frame. Although a normal state can serve as a baseline, it need not be a state or condition that the user actually was in at any particular time. It may, for example, merely represent a goal or target. A "normal" state can be defined or selected by the user or user of the ketone measurement device or, for example, the physician prescribing the ketone measurement and overseeing the use of the measurement or analysis device.

A "baseline" can be but need not be a "normal state." In the context of a diet program, for example, the weight at the beginning of the diet may be selected as the baseline, and the "normal state" of the user may be the target weight to be achieved during the program. Alternatively, the baseline may be the weight at the beginning of the program, and the target weight for the completion of the program may be well above what might be considered a "normal" weight for that user. A series of programs, in that illustrative case, may be required to achieve the "normal" state.

"Normal state information" is data or information, e.g., such as an analyte concentration, a physiological state, an ambient condition, or the like, that characterizes or describes the normal state. Normal state information generally comprises a quantitative value, a statistical measure such as a mean value, or other quantitative measure. It may, however, comprise a physical or physiological state, such as tall, short, heavy, slender, and so on.

In accordance with various aspects of the invention, variables, associated parameter data and associated compensation factors can be segregated into classes.

Although some generally are not considered a variable for purposes of a ketone analysis, one class of information that is collected and associated with other variables or data is information or data that serves to identify the user. Examples would include the user's name, often a user identification number, the user's birth date, age, gender and ethnicity. With limited exceptions, such as age, these data do not typically change for a given user, and thus generally would not be considered variables or have associated parameter data. There are some, however, that do, e.g., such as age, and may serve as useful candidates for parameter data and use in compensation. In addition, some may change from user to user and provide valuable population variables or data.

Another class of variables pertains to the condition or state of the user himself or herself. These user-specific variables can be an important class and often are the most important of variables to consider and accommodate. User-specific variables or factors can be further divided into subclasses, e.g., such as physical factors, lifestyle factors, and physiological or pathophysiological factors.

The physical factors subclass within this user-specific class would include, for example, physical factors of the user, such as his or her height, weight, body mass index (BMI), and the like.

Lifestyle factors pertain to the lifestyle of the user, which may have important implications for interpreting measurements and trends, and for predicting future trends. Examples of lifestyle factors include general diet, physical activity level (e.g., exercise, sedentary versus non-sedentary job), general stress level, tobacco usage, alcohol usage, prescription medications, dietary supplements, etc.

Another subclass of variables comprises physiological and pathophysiological factors, for example, such as current wellness, illness, disease, injury or condition, heart condition, issues with kidneys or urinary tract, lung capacity, barriers to transport in the lungs (e.g., alveolar wall thickness), and the like. These factors also would include things like user activity level (e.g., sedentary, highly active), smoker versus non-smoker, and for women, pregnancy or menstrual cycle. Parameter data useful in quantifying such factors would include, for example, pulse or heart rate, blood pressure, blood pH, anemia, breathing rate, airway resistance, resting metabolic rate, oxygen uptake, etc.

Another class of variables pertains to environmental factors, pertaining to the environment in which the ketone measurement is taken. Examples of environmental factors include the time of day when the ketone measurement is performed, the geographic location of the measurement, ambient conditions such as temperature, pressure, altitude, and the like. The geographic location of the analysis can have a significant impact on measured analyte values. The geographic location, for example, can have an important impact on such ambient conditions such as temperature, pressure, altitude, and the like. Altitude, for example, is a well-known factor influencing such physiological functions as hydration and dehydration, and gastrointestinal function. Geographic information taken together with date or seasonal information can be used to generate compensation factors that address a combination of variables, such as, e.g., average or likely temperature, average length of sunlight (impacting mood and stress levels, for example).

Still another class of variables, parameter data and compensation factors pertains to the measurement analysis device itself and its use in connection with the ketone measurement or analysis. Examples would include the specific model of the device, its manufacturing and service data or history, its last calibration, and the like.

Another class of variables, parameter data and compensation factors pertains to the ketone measurement itself. Examples would include the date and time the measurement was taken, specific protocols used to conduct the measurement, and the like. In some ketone measurements, and particularly with breath acetone measurements, the protocol or protocols used to collect the sample and measure the analyte can be particularly important.

A sample collection protocol, for example, is a protocol by which a sample of the fluid is collected for measurement. Examples of breath collection protocols would include such things as direct input of the breath by blowing into the device as opposed to an indirect method such as use of a breath sample bag; in the latter instance, the duration of time that the breath sample remains in the bag before the ketone measurement is made; etc. Breath collection protocols also might include the breathing regime used by the user in providing the breath sample, such as where the breath collection is based on a single exhalation, multiple exhalations, multiple breaths (inhalation and exhalation), rebreathing, and the like.

A sensing protocol is a protocol used in the process of sensing or measuring the sample to detect and measure the analyte or analytes of interest in the fluid. Examples of a sensing protocol or portions thereof would include the timing of capturing optical changes in a colorimetric reaction or the operating temperature of a metal oxide sensor.

A processing protocol is a protocol is used to process the signal or signals obtained as a result of the sensing. Examples of a processing protocol or portions thereof would include the method by which raw optical images are processed (e.g., for color intensity, using a CIEDE algorithm or others) or the method by which raw signal data from a metal oxide sensor is converted into a concentration (e.g., kinetic versus equilibrium analysis, etc.)

"Population Data" is used broadly to mean qualitative or quantitative information pertaining to the aspect of the relevant analyte or measurement that is being reported, where the information has been collected from a plurality of individuals. Such information is often useful to establish population reference ranges, trends or changes, or predictions. It may be desirable for the plurality of individuals to represent a statistically significant sample, for example of a particular ethnicity, sex, health status, or other stratifying characteristic.

In accordance with another aspect of the invention, preferred systems and method implementations may comprise the storage and/or use of "population data" to compensate for variables or factors, e.g., such as those outlined herein above. In some applications, as an alternative to or in addition to user-specific parameter information derived from the specific user whose breath is being analyzed, it is useful or even necessary to use similar data from a multiple-user population, or statistical data.

Population data typically comprises but is not necessarily limited to statistical data obtained from significant numbers of trials, clinical inputs, measurements, etc. of one or more of the variables and variable classes outlined herein above.

Population data aids in establishing parameters or compensation factors such as normal variability, ranges of acceptable and pathological values, and trends. Population data can provide statistically-derived compensation information and compensation factors that utilizes data or information from sources other than the specific user whose ketone levels are being measured.

It requires considerable time and effort to understand how best to investigate and use new analytes most meaningfully. Great advantage can be obtained from mechanisms by which data can be collated from a large group of users, which data then can provide a means by which more customized guidance can be periodically provided to the user population or healthcare providers. This data collection not only aids in obtaining better and more accurate information, but also aids in applying the data and related discoveries to provide better clinical outcomes. The present inventors believe that advantages of the invention in its various aspects, embodiments and implementations will provide great value into the future, for example, by generating and aggregating high-resolution analyte data under varying demographics (e.g., ethic, gender, age, activity level, etc.) or under different health conditions (e.g., renal failure, emphysema, COPD, etc.), and through associated trending data to help provide more customized correlations and feedback to users and treating physicians.

To provide an example, it is desirable to measure breath acetone levels for a host of different purposes, including: (a) adherence to a ketogenic diet for cancer management, (b) adherence to a ketogenic diet for epilepsy management, (c) detecting, monitoring and/or preventing diabetic ketoacidosis, and (d) monitoring adherence to a diet or exercise program. The range of "normal" acetone values varies from condition to condition. Population data thus can be helpful in determining "normal" and aberrant levels.

As another specific but merely illustrative example, when conducting a series of breath analyses over time for a user involved in a weight loss program, there may not be (and probably is not) a "normal" or expected breath acetone level for that particular user at week X, for example. The user, however and for example, can use population data in the form of acetone levels from past or present user populations in the same or similar weight loss programs at week x to obtain an average, normalized or expected breath acetone level.

Additional examples of information derived from population data are set forth in Table 1.

TABLE 1

Examples of Information Derived from Population Data

| | |
|---|---|
| A | Best time of day to measure acetone levels |
| B | Amount of time before meal to perform measurement |
| C | Amount of time before exercise to perform measurement |
| D | Importance of holding breath before measurement |
| E | Requirements for the user to be at rest |
| F | Volume requirements for exhaled breath sample |
| G | Diseases that may affect the relevance of the output |
| H | Units that better correlate to the underlying physiological phenomenon (e.g., ppm versus ppm/second) |
| I | Increase/decrease the frequency of your use of the device |

Figure 4:
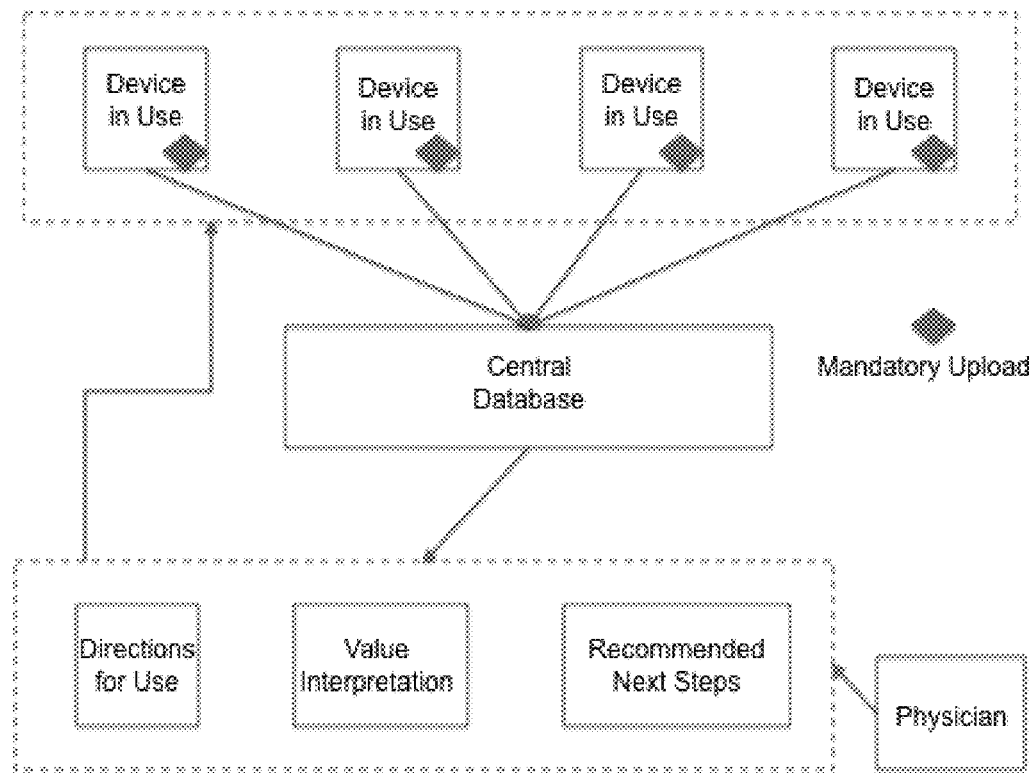
FIG. 4 shows a block diagram of data and information flows for certain preferred embodiments and method implementations according to aspects of the invention.

Population data can also be used to provide improved directions to the user on how to use the measurement device. FIG. 4 presents a general block diagram for use of population data.

Having discussed various classes of variables and associated parameter and population data, it is useful and in some instances important to consider a grouping of variables or data referred to herein as "measurement state information" or equivalently "measurement state data." The "measurement state" refers to the state of the user and the surrounding or applicable conditions and circumstances at the time and place where the ketone measurement is made, or a reasonable approximation of it. "Measurement state information" comprises data or information that describes or helps to characterize the measurement state.

The measurement state normally will be at or about the time the breath is inputted into the breath analysis device for measurement, although this need not be the case. For reasons that will be further explained herein below, one normally wishes for the measurement state to reflect the user's state or condition at the time the fluid sample is created. The specific state or condition can be any one or combination of a variety of factors or circumstances that are expected may vary from the "normal state."

It should be noted that both normal state information and measurement state information may pertain to or comprise not only user-specific parameter information, but also to other information such as environmental factors and ketone analysis device-related factors. As with normal state information, measurement state information may comprise quantitative data or information, qualitative information, etc.

General Methods for Measuring Ketones Using Compensation Factors

In view of the foregoing, preferred systems and method implementations that use compensation factors according to aspects of the invention to improve ketone measurement will now be discussed.

A presently preferred method implementation according to the invention comprises the following:
(1) Establish the regime for ketone testing:
 (a) Determine the fluid or fluids that will be analyzed for ketone concentration,
 (b) Select the system that will be used to measure the ketone concentrations,
 (c) Establish or ascertain the protocols that will be used in the sample collection and analysis;
(2) Anticipate compensation variables and prepare for their compensation:
 (a) Identify and anticipate the variables (compensation variables) that are likely to be encountered in the testing,
 (b) Establish corresponding compensation factors or means to obtain compensation factors,
 (c) Pre-position or pre-deploy the data, processing algorithms, processing capability and communications links to appropriately and timely generate and/or apply the compensation factors;
(3) As the ketone measurement tests are conducted, identify applicable variables and apply compensation factors:
 (a) Use the selected ketone measurement system or systems to obtain the ketone measurement results,
 (b) As a pre-planning measure and/or as part of the ketone measurements, identify the variable or variables that are encountered in the testing,
 (c) Use the pre-positioned or pre-deployed data, processing algorithms, processing capability and communication links to appropriately and timely generate and/or apply the compensation factors,
 (d) Optionally apply the compensation factor or factors to the measurement results to obtain appropriately modified or compensated results, and
 (e) Output the modified measurement result, or the measurement result and the appropriate compensation factors.

Another presently preferred method implementation comprises the following:
(1) Establish a baseline or "normal state";
(2) Establish protocols, e.g., for fluid sample collection, sensing and processing;
(3) Identify variables that are to be addressed (compensation variables), which may include, for example, user-specific factors (e.g., physical factors and/or physiological & pathophysiological factors), and so on;
(4) Provide and preferably selectively pre-store parameter data and/or population data for the compensation factor or factors;
(5) Conduct the ketone measurement from the fluid sample and obtain a measurement signal; and
(6) Apply compensating factor or factors to the measurement signal, identify the compensation factor or factors, plot them, transmit them, or otherwise associate them with the measurement signal.

In view of the description to this point, it is clear that the particular system or systems used in making the ketone measurement and the specific protocols used in operating those systems and conducting the ketone measurement tests can bring to bear their own set of variables. To explain, better understand and appreciate, and address such variables, systems that are designed to analyze specific body fluids, namely blood, urine and breath, will now be described.

Figure 5:
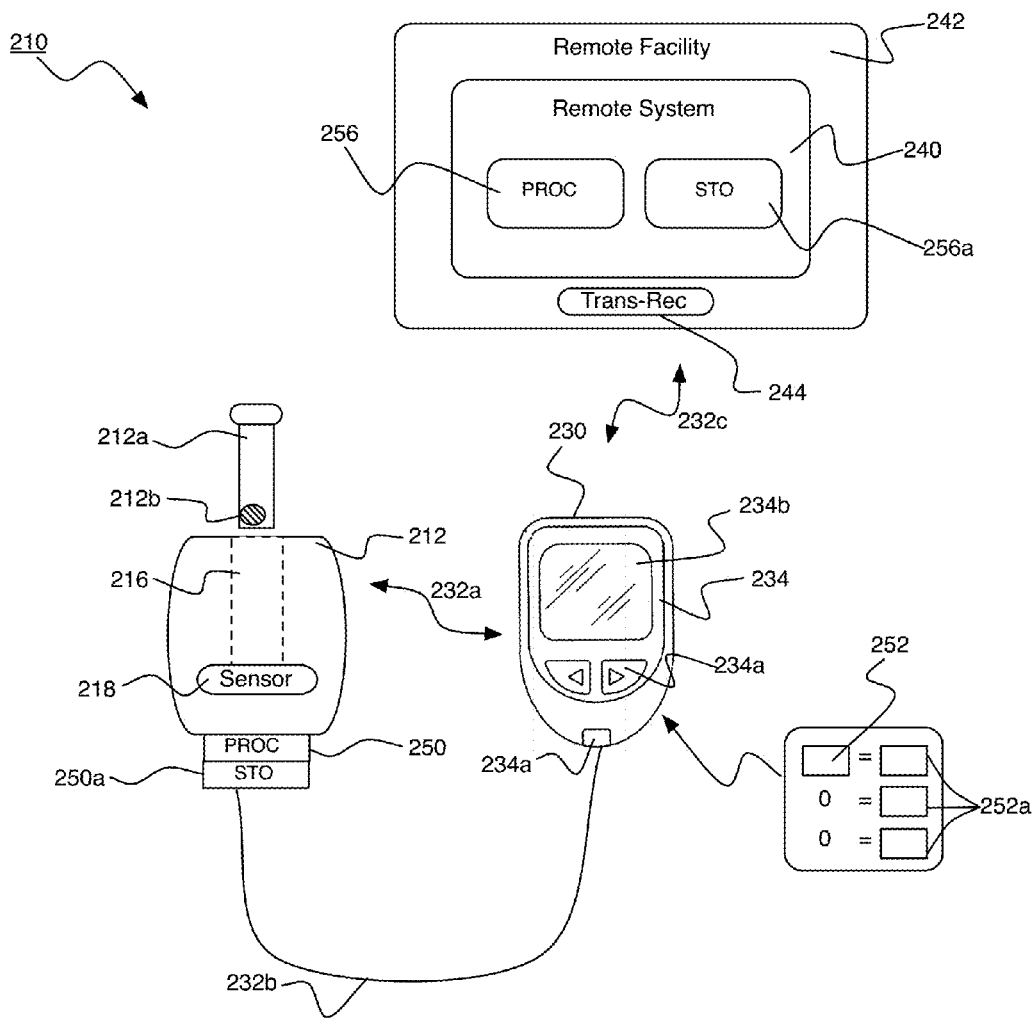
FIG. 5 shows a system for measuring one or more ketones in the blood of a user in accordance with a presently preferred embodiment of another aspect of the invention.

With reference to FIG. 5, a system 210 according to another preferred embodiment, this one adapted for measuring one or more ketones in the blood of a user, is shown. As noted herein above, ketones in blood typically include acetoacetate and β-HB.

System 201 comprises a portable blood ketone measurement device 212 that measures the concentration of the ketones in a blood sample from the user. Measurement device 212 in this presently preferred embodiment comprises a blood ketone meter, including associated ketone test strips 212a, commercially available from Abbott Laboratories, Inc. of Chicago, Ill. In accordance the published instructions for the commercial blood ketone meter, the user or user prepares the blood sample by piercing the skin at a fingertip of the user to create a visible droplet of blood on the skin, and then places a distal end 212b at the fingertip location so that the blood droplet is adsorbed onto or absorbed into the test strip material at distal end 212b. The test strip 212a is then inserted into a fluid sample input in the form of a receiving cavity 216 in measurement device 212—distal end 212b first—so that the blood sample at test strip distal end 212b is detachably secured measurement device 212 in operative communication a sensing subsystem 218.

Sensing subsystem 218 comprises a range of devices and technologies that are capable of measuring relevant concentrations of ketones in blood, and are amenable to use in a portable measurement device. An example of such sensing subsystem would be electrochemical detection of beta-hydroxybutyrate in blood.

An example of an integrated device is shown in FIG. 17. Here, the user 950 uses a lancet 900 to prick his or her finger 910 to obtain a drop of blood. The blood is deposited to a test strip 920, which is inserted into a meter 930. The same meter can be coupled to a mouthpiece 940, which the user 950 can exhale through as shown in FIG. 17D.

Other examples are provided in U.S. patent application Ser. No. 12/228,046, commonly owned by the assignee.

Figure 7:
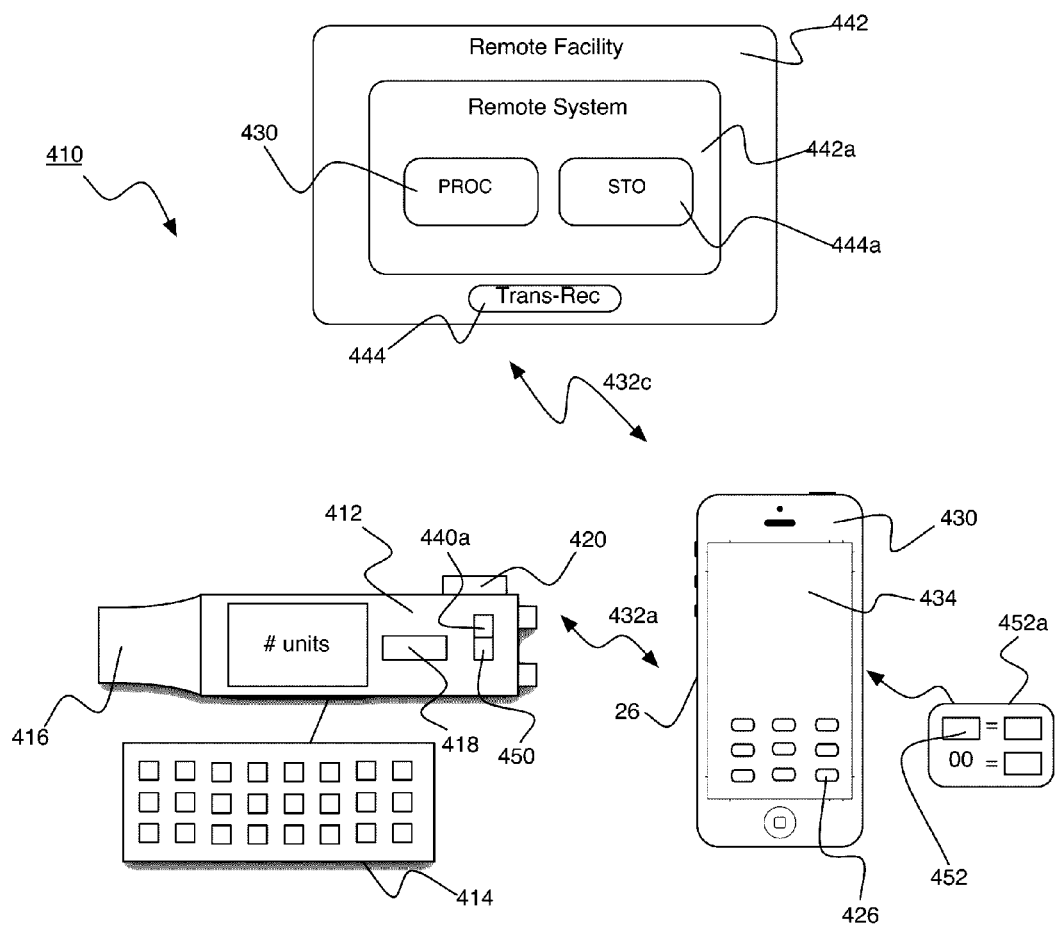
FIG. 7 shows a first system for measuring acetone in the breath of a user in accordance with a presently preferred embodiment of another aspect of the invention.

System 210 also comprises a communications device 230 in operative communication with measurement device 212, as illustrated in FIG. 7 by wireless connection 232a, with optional cable 232b. In system 210, the communication device 230 is the same POCED device 130 as shown in FIG. 2 and described herein above, with the same wireless links. It also comprises a processor 252 and storage 252a, which are the same as processor 152 and storage 152a of system 110. Moreover, POCED 230 is loaded with the App described herein. Communications device or POCED 230 also embodies the same communications equipment and features as described herein above with respect to device 130, and is adapted to receive a measurement signal from measurement device 212.

Both measurement device 212 and communications device 230 are located at a first location, which preferably comprises a location at which a user of the system, such as the user whose ketone levels are being measured is located, e.g., at the user—user's home or workplace, as discussed herein above.

System 210 further comprises a remote system 240 disposed within a remote facility or center facility 242 at a second location remote from the first location. In system 210, remote system 240 and remote facility 242 are fully equivalent to remote system 140 and remote facility 142 of system 110, shown in FIG. 2 and described herein above.

POCED 230 and remote system 240 are in operative communication, e.g., as illustrated by wireless link 232b. With connections or communication links as here, measurement device 212, communications device 230 and remote system 240 are configured to communicate data, preferably but optionally bi-directionally, preferably including the measurement signal and additionally parameter data as described more fully herein below.

System 210 can be used according to a presently preferred method implementation to measure the blood ketone levels of a user as illustrated in the following examples. It will be appreciated, however, that the method is not necessarily limited to conduct using system 210, and that other systems may be used to perform the method.

Figure 6:
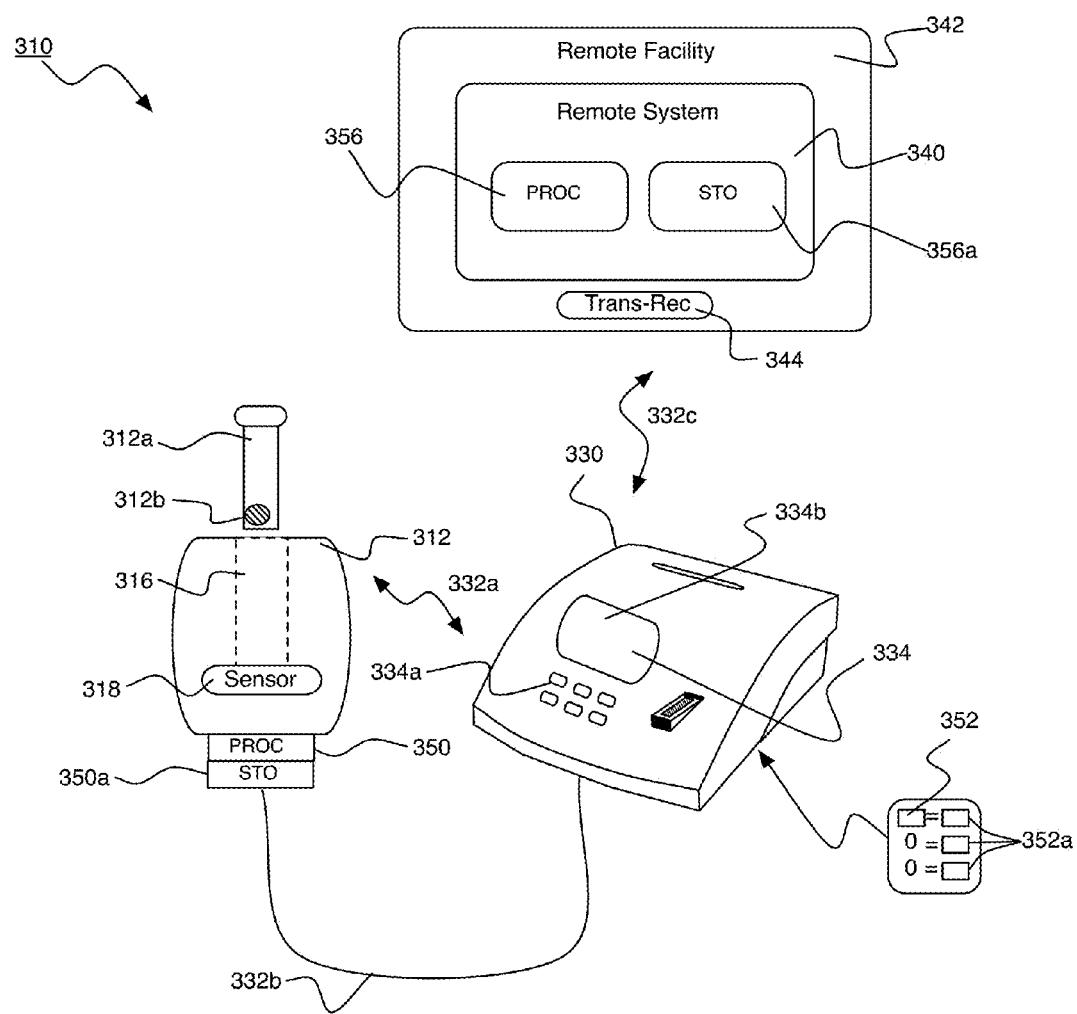
FIG. 6 shows a system for measuring one or more ketones in the urine of a user in accordance with a presently preferred embodiment of another aspect of the invention.

Turning now to FIG. 6, a system 310 according to another preferred embodiment, configured to measure one or more ketones in the urine of a user, is shown. Ketones typically found in urine, as discussed herein above, include acetoacetate and β-HB.

System 310 comprises a portable urine ketone measurement device 312 that measures the concentration of the ketones in a blood sample from the user.

Measurement device 312 in this presently preferred embodiment comprises a urine ketone meter that employs Ketostix® urine ketone test strips 312a, commercially available from Bayer. In accordance the published instructions for the commercial Ketostix® test strips, the user or user prepares the urine sample blood sample by obtaining a urine sample, and by submerging a distal end 312b of the strip 312 into the urine sample (not shown) so that the urine is adsorbed onto or absorbed into the test strip material at distal end 312b. The test strip 312a is then inserted into a fluid sample input in the form of a receiving cavity 316 in measurement device 312—distal end 312b first—so that the urine sample at test strip distal end 312b is detachably secured measurement device 312 in operative communication a sensing subsystem 318.

System 310 also comprises a communications device 330 in operative communication with measurement device 312. In system 310, the communication device 330 is the same POCED device 130 as shown in FIG. 2 and described herein above, with the same wireless links. It also comprises a processor 352 and storage 352a, which are the same as processor 152 and storage 152a of system 10. Moreover, it is loaded with the App described herein above. Communications device 330 embodies the same communications equipment and features as described herein above with respect to device 130, and is adapted to receive a measurement signal from measurement device 312, also as described herein above.

Both measurement device 312 and communications device 330 are located at a first location, which preferably comprises a location at which a user of the system, such as the user whose ketone levels are being measured is located, e.g., at the user—user's home or workplace.

System 310 further comprises a remote system 340 disposed within a remote facility or center facility 342 at a second location remote from the first location. In system 310, remote system 340 and remote facility 342 are fully equivalent to remote system 140 and remote facility 142 of system 110, shown in FIG. 2 and described herein above.

With connections or communication links as described herein above with respect to breath analysis device 112, communications device 130 and remote system 140, system 310 is configured to communicate data, preferably but optionally bi-directionally, preferably including the measurement signal and additionally parameter data as described more fully herein below.

System 210 can be used according to a presently preferred method implementation to measure the blood ketone levels of a user as illustrated in the following examples. It will be appreciated, however, that the method is not necessarily limited to conduct using system 210, and that other systems may be used to perform the method.

A system 410 according to another presently preferred embodiment of the invention is shown in FIG. 7. System 410 is configured to measure acetone in the breath of a user, typically in the form of a breath sample.

System 410 comprises a breath analysis or measurement device 412. Presently preferred breath acetone measurement devices are those shown and described in U.S. Patent Provisional Application No. 61/800,081, which is hereby incorporated herein by reference as if fully set forth herein.

Measurement device 412 comprises a fluid sample input in the form of a mouthpiece 416, into which the user may blow or exhale directly to input a breath sample. It further comprises a sensor or sensing system 418 in fluid communication with input 416 so that the breath sample contacts or interacts with the sensing system, whereupon sensing system 418 measures the concentration of the acetone in the breath sample and generates a measurement signal representative of that acetone concentration. The sensing system may be as described herein above. Measurement device 412 further comprises a processor 450 and associated storage 254a. Processor 450, which may comprise the same structure as processor 50 in system 10, is operatively coupled to sensing system 418 so that processor 50 receives the measurement signal from sensing system 418 and stores it in storage 450a. Processor 450 then causes a measurement device communications subsystem 419, which is identical to or the equivalent of communications subsystem 19 in system 10, to transmit the measurement signal.

System 410 also comprises a communications device 430 in operative communication with measurement device 412. In system 410, communication device 430 is the same POCED device 130 as shown in FIG. 2 and described herein above, with the same wireless links. It also comprises a processor 452 and storage 452a as processor 152 and storage 152a of system 110. Moreover, it is loaded with the App described herein. Communications device 430 includes the same communications equipment and features as described herein above with respect to device 130, and is adapted to receive the measurement signal from measurement device 412.

Both measurement device 412 and communications device 430 are located at a first location which, as previously described, preferably comprises a location at which a user of the system, such as the user whose ketone levels are being measured is located, e.g., at the user—user's home or workplace.

System 410 further comprises a remote system 440 disposed within a remote facility or center facility 442 at a second location remote from the first location. In system 410, remote system 440 and remote facility 442 are fully equivalent to remote system 140 and remote facility 142 of system 110, shown in FIG. 2 and described herein above.

With connections or communication links as described herein above with respect to breath analysis device 412, communications device 430 and remote system 440, system 410 is configured to communicate data, preferably but optionally bi-directionally, preferably including the measurement signal and additionally parameter data as described more fully herein.

Figure 8:
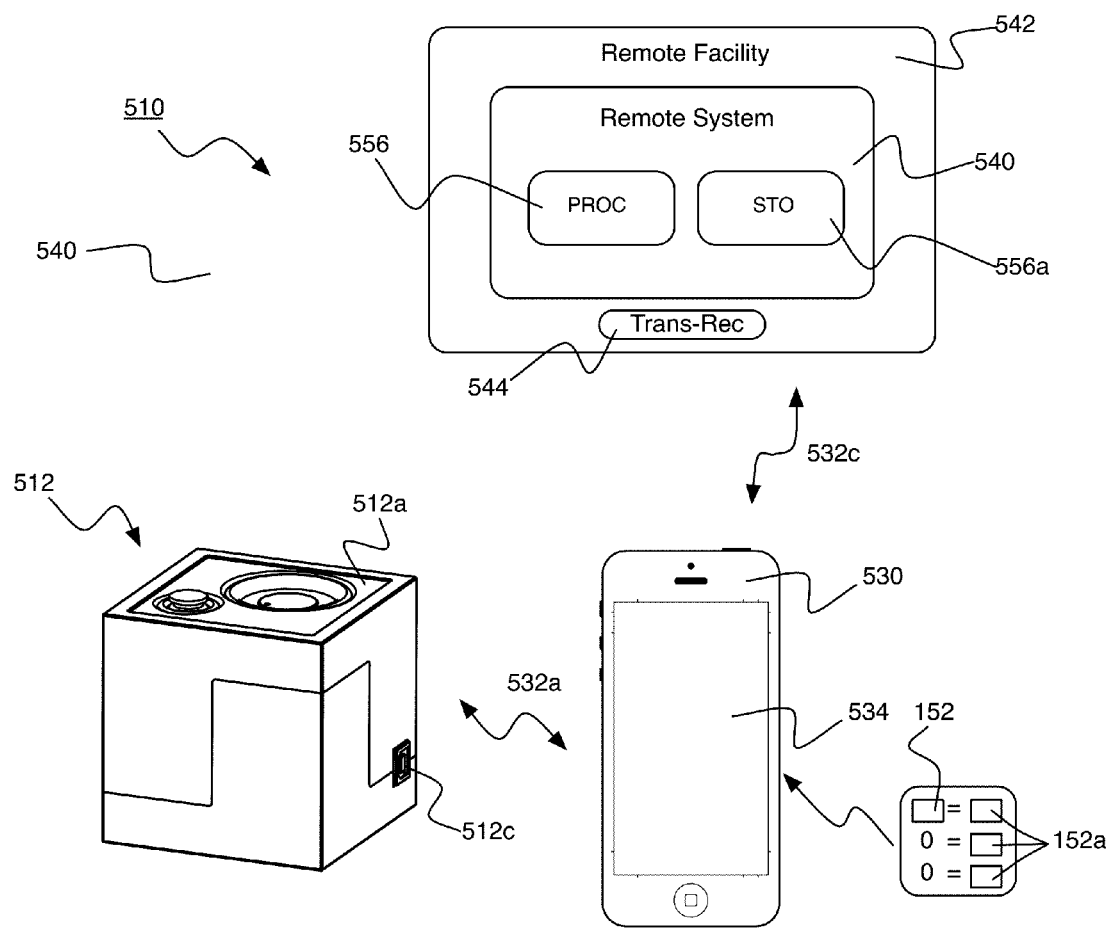
FIG. 8 shows a second system for measuring acetone in the breath of a user in accordance with a presently preferred embodiment of another aspect of the invention.
Figure 9:
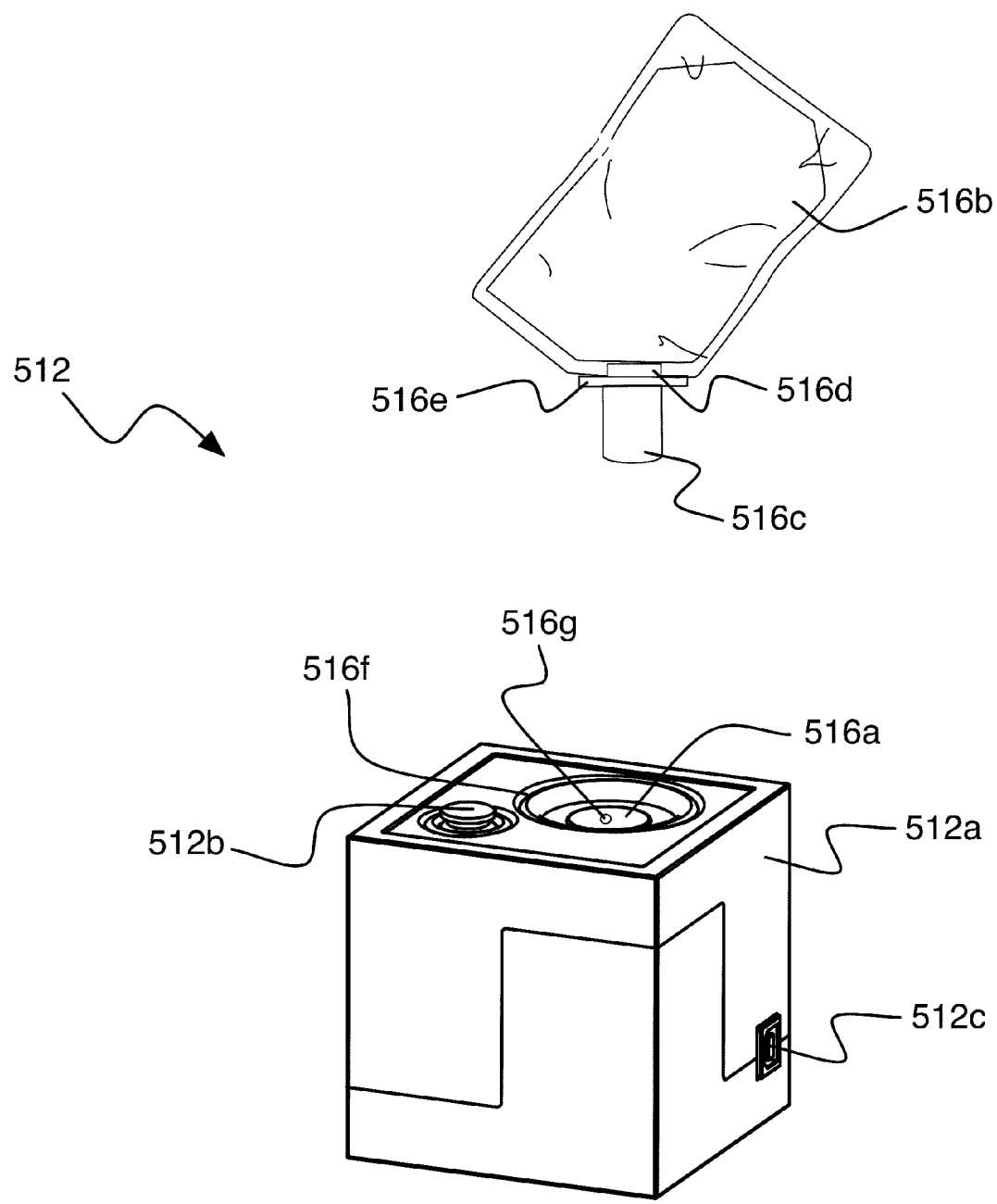
FIG. 9 shows a perspective view of a presently preferred breath acetone measuring device that is part of the system of FIG. 8.
Figure 10:
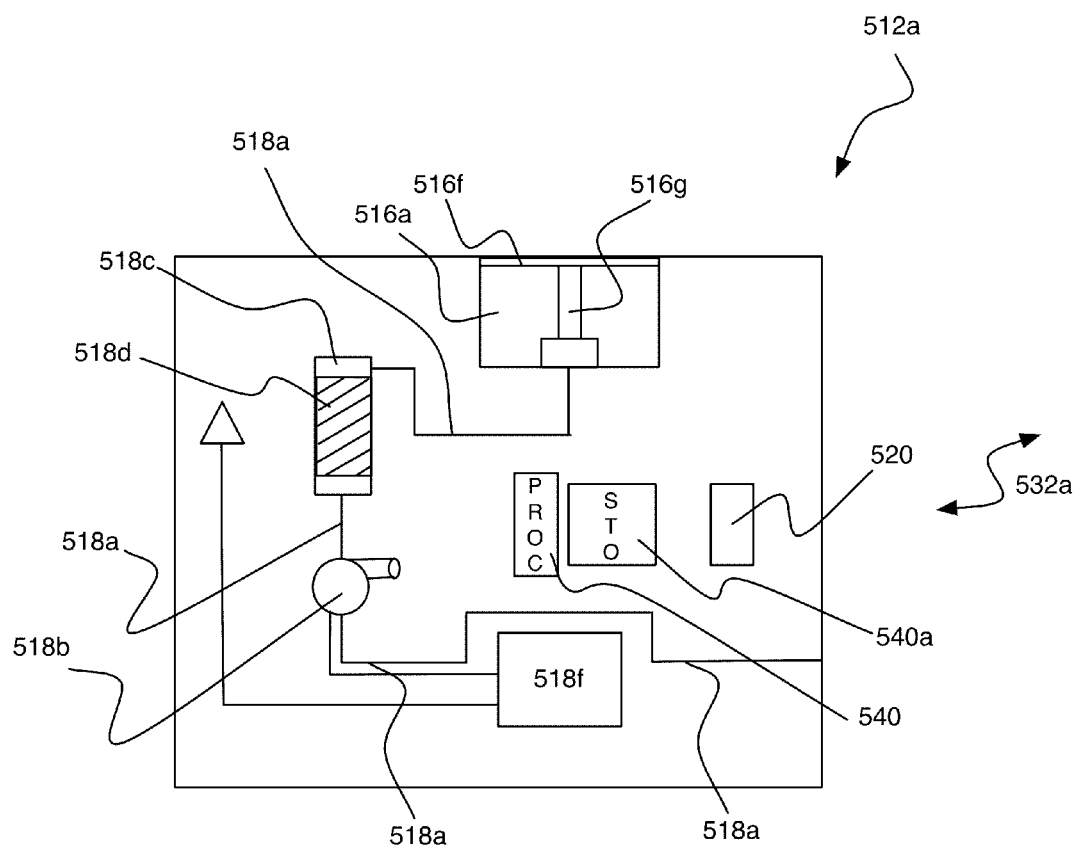
FIG. 10 shows a side cutaway view of the base of the breath acetone measuring device shown in FIG. 9.

A system 510 according to still another presently preferred embodiment of the invention is shown in FIGS. 8-10. System 510 also is configured for measuring acetone in the breath of a user. With reference to FIG. 8, system 510 comprises a breath ketone measurement device 512, a communications device 530, which in this embodiment comprises the same POCED as POCED 130 in system 110 of FIG. 2, and a remote system 540 identical to remote system 140 of system 110 in FIG. 2. The related components and communications links as shown in previous drawing figures and described herein above apply to this system as well, as indicated by the same or like reference numerals. Other than the substitution of a different ketone measurement device, system 510 actually is similar to or exactly the same as system 410 of FIG. 7.

As shown in FIG. 9, breath acetone measurement device 512 of system 510 comprises a base or base unit 512a. Base 512a comprises a power button 512b and an input port 516a.

Device 512 further comprises a breath sample bag or breath bag 516b that includes a bag mouthpiece and ferrule 516c and one-way valve 516b. Breath bag 516b is a physically separate component relative to base 512a, but is adapted to detachably couple to base 512a by coupling breath bag ferrule 516c into base input port 516a so that they seal in a fluid-tight manner. This coupling preferably is confirmed by a switch that is electrically coupled to a microprocessor.

In use, initially breath bag 516b is detached from base 512a and is fully deflated. The user places his or her mouth at the bag mouthpiece 516c and blows into bag 516b to inflate it with a sample of the user's breath. One-way valve 516d allows the breath sample to enter bag 516b, but prevents it from escaping back out mouthpiece 516c, thus retaining the breath sample in the bag.

The user then places the inflated breath bag 516b onto base 512a by inserting ferrule 516c into base input port 516a. As this mating occurs, one-way valve 516d is pressed onto a post 516g disposed in base input port 516a, which biases a flap in the one-way valve and opens it so that the breath sample is released from the bag 516b and can freely enter base input port 516a.

With reference to FIG. 10, which shows a cross-sectional cutaway side view of base 516a, the breath sample from breath bag 516b, upon entering base 512b through input port 516a, is directed along a flow path 518a under the influence of a pump 518b to the sensing system 518. Sensing system 518 comprises a detachable cartridge 518c that in turn comprises a chemical interactant 518d that reacts with acetone in the breath sample to cause a color or chromatic change in the cartridge that is representative of the concentration of acetone in the breath sample. A camera 518e that is sensitive to the colorimetric or chromatic change senses the change present in the cartridge as a result of the breath sample exposure, and communicates that sensed change as a measurement signal to a sensing system circuit board 518f. Circuit board 518f performs routine signal conditioning and formatting on the measurement signal and communicates it to processor 550, which stores it in storage 550a. Processor 550 then transmits the measurement signal to communications device 530 using transceiver 520 (which is identical to or the equivalent of transceiver 120 in system 110).

Processor Configurations and Communications Options

In accordance with presently preferred systems and methods, as the ketone measurement is made (as it is made or shortly before or after), the measured ketone level is analyzed with or against parameter data relating to one or more variables, e.g., user-specific data, environmental data, measurement device data, measurement data, etc., and the measured level is modified as appropriate according to one or more compensation factors to correct the measured level for unwanted effects of the one or more variables.

Given the design and configuration of preferred systems according to the invention, and the methods of modifying the measured ketone levels using compensation factors, there are several options regarding: (a) where in the system the parameter data is stored, and (b) where in the system the processing associated with the methods is performed. Each of the main hardware components of the presently preferred system embodiments and methods presented herein—comprising the ketone measurement device, the communications device and the remote system—can be equipped with one or more processors and processing capability, including associated storage, to store part or all of the parameter data and population data, and to perform the processing necessary and appropriate to successfully conduct and complete the methods. Thus, all or virtually all of the storage and processing capability could be located at any one of these main hardware components. Alternatively, either the storage or the processing or both could be divided up among the main components. The transmission links between each of the main components, whether directly connected, wired, wireless or otherwise, have sufficient capacity to transmit the measurement signal, the parameter data and associated data, addressing or overhead to enable appropriate the measurement signal and/or parameter data to be made available at the processing site so that the compensation factors analysis can be timely applied.

Thus, the decision of where to locate the storage and processing functions among system components can be made on an application-specific basis and tailored to meet system and method objectives in each specific application. The flexible decision making process can take advantage of efficiencies and benefits inherent in a specific system design or component, while avoiding limitations and risks in that intended application. Where system components are selected, for example, in system embodiment 110, such that the inherent availability, processing power and features of POCED 130 are employed, one need not design ketone measurement device 112 with more storage and processing power than is needed to perform the ketone measurement, generate the measurement signal, and transmit it to POCED 130. Where the volume or perishability of the parameter data or population data is high, one may maximize the efficiency of the system by positioning it at remote system 140, where a fixed location and potentially greater storage and processing capability can be employed through a fixed location (remote facility 142) that has physical space, power, and staffing to manage it, and from where it can be made readily available to be transferred on demand to POCED 130.

Given the flexibility of preferred systems and methods that implement the inventive designs, an illustrative means or example for configuring specific preferred applications is provided in Table 2.

TABLE 2

Data Pre-Storage Allocation

| VARIABLE | MEASUREMENT DEVICE | COMMUNICATIONS DEVICE | REMOTE SYSTEM | NOTES |
|---|---|---|---|---|
| USER ID | | | | |
| Name or ID | | X | | |
| Birth Date | | X | | |
| Age | | X | | |
| Gender | | X | | |
| Ethnicity | | X | | |
| USER-SPECIFIC STATE DATA | | | | |
| General Physical Data | | | | |
| Height | | X | | |
| Lung capacity | | X | | |
| General Lifestyle Data | | | | |
| Physical activity level | | X | | |
| Tobacco usage | | X | | |
| Generally Transient Lifestyle or Physical Data | | | | |
| Weight | | X | | |
| BMI | | X | | |
| Current wellness | | X | | |
| Chronic issues | | X | | |
| Disease issues | | X | | |
| Stress level | | X | | |
| Heart rate | | X | | |
| Exercise | | X | | |
| Alcohol | | | | |
| ENVIRONMENTAL DATA | | | | |
| Location | | | | |
| Geophysical location | X | X | | |
| General climate | X | X | | |
| General air quality | X | X | | |
| Altitude | X | X | | |
| Ambient Conditions | | | | |
| Temperature | X | | | |
| Humidity | X | | | |
| Barometric pressure | X | | | |
| Air quality | X | | | |
| MEASUREMENT DEVICE DATA | | | | |
| Device ID | X | X | | |
| Configuration | X | | | |
| Maintenance history | | | | |
| Operational issues | X | | X | |
| Calibration information | X | | X | |
| Software-Firmware | | | | |
| Version/Updates | X | X | X | |
| MEASUREMENT DATA | | | | |
| Consumable Components | | | | |
| ID | X | | | |
| Specifications | X | X | | |
| Analyte Data | | | | |
| Analyte measured | X | | | |
| Sensitivity range | X | | | |
| Measurement Protocols | | | | |
| Fluid collection protocol | X | X | | |
| Sensing protocol | X | X | | |
| Processing protocol | X | X | | |
| POPULATION DATA | | | X | |

In Table 2, the first column lists the classes and subclasses of variables and corresponding parameter data and population data that are to be considered or addressed in the particular application, each of which is represented in the respective rows of the table. The second column of Table 2 is for designation of the various classes and subclasses of parameter data and population data that are to be pre-stored in the memory or storage of the measurement device. Similarly, the third and fourth columns of Table 1 are for designation of the various classes and subclasses of parameter data and population data that are to be pre-stored in the memory or storage of the communications device (e.g., POCED) and remote system, respectively. The "x" designations in Table 2 provide an illustrative example of actual data allocations for presently preferred system embodiments and methods. Many other allocations, of course, are possible.

Using Table 2, a designer of an application of system 110, for example, may select the variables that are to be considered from those listed in the first column. Armed with a knowledge of the processing and storage capacity of each of the main system components and the parameter data associated with the selected variables, the designer then may carefully consider where and how to allocate those data in pre-storage among the components to achieve the objectives of the system design, e.g., minimize response time, minimize data transfer requirements, maximize system accuracy, maximize system reliability, and the like.

The actual inputting of data into the various storage devices as heretofore described may be accomplished by a variety of known means.

The initial input of parameter and/or population data into system components typically comprises bulk data input. Examples include wireless or hardwired data transfers, e.g. via network, the Internet, etc., or transfers from mass storage devices, such as an external hard drive, flash drive, compact disk, DVD, and the like.

In preferred system embodiments and methods, certain of the parameter data is inputted or provided automatically by one or more system components or associated systems.

In presently preferred embodiments of the ketone measurement devices, for example, measurement device data and measurement data are pre-stored in the ketone measurement device itself. Part or all of that data optionally may be communicated to the communications device with each measurement (e.g., with each measurement signal), periodically, or according to some other method or protocol. Similarly, part or all of the measurement device data and measurement data may be pre-stored at the communications device. In this latter instance, the measurement device may only transmit a signal confirming this data or indicating any changes, rather than providing the data itself. Alternatively, it may be presumed by the communications device that the measurement device data and measurement data have not changed relative to the data pre-stored in the communications device, except when a signal from the measurement device indicates that a change has occurred.

In addition to measurement device data and measurement data, the measurement device and/or the communications device may be and preferably are configured to automatically tag a measurement signal with a time and date for the measurement using built-in clock and calendar functions. Optionally, a location for the test may and preferably is tagged with the measurement signal, which may be automatically supplemented from geographic and meteorological data (e.g., subsequently at the remote system or at the measurement device or the communications device using data provided by it) to impute altitude, ambient air quality and weather conditions, and the like.

In certain applications and system configurations, it may be desirable or even necessary to enter parameter data manually, particularly when the data relates to or is affected by highly-ephemeral or perishable circumstances. Examples of such ephemeral data include a user's activities immediately preceding a ketone measurement, e.g., such as exercise, meal or beverage consumption, drug administration, or the like. Similarly, user-specific physical or pathophysiological conditions such as heart rate, illness (e.g., cold or flu symptoms), etc. can be inputted manually, with or without the assistance of an external device such as a separate heart rate monitor. Certain environmental factors that the system is not configured to automatically record also would be examples of ephemeral data, such as sun or rain, ambient temperature, general air quality, raining versus non-raining conditions, wind conditions, and so on. In such instances, the user may manually enter such data into the system at or contemporaneously with the time of ketone measurement. This may be done, for example, using unit 11 touchpad 36 of system 10 (FIG. 1), or measurement device 112 touchpad 114 or POCED touchpad 36 in system 110 (FIG. 2), and their counterparts in the subsequent preferred systems shown in subsequent drawing figures.

Figure 11:
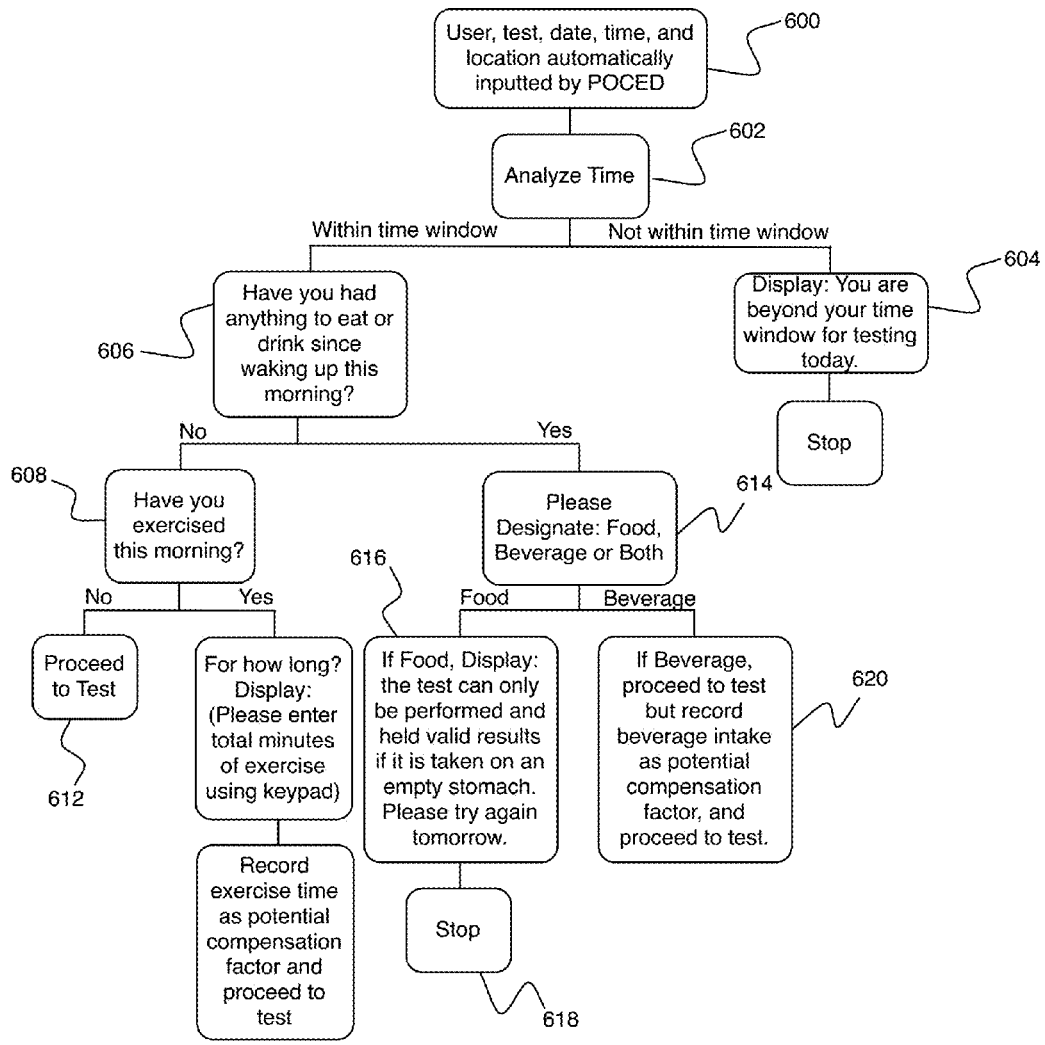
FIG. 11 is a process flow diagram illustrating a process for measuring one or more ketones in the one or more bodily fluids according to a preferred implementation of another aspect of the invention.

In addition to the foregoing data input methods, preferred systems and methods also may input data manually, albeit using a software app and associated prompting. An illustrative example of such app-associated data input involves the inputting of measurement state information. A presently preferred but merely illustrative example of this software-managed or guided input method is provided in FIG. 11, which for illustrative purposes is carried out using system 110 of FIG. 2.

As generally described herein above, at least a portion of the measurement state information has been entered into measurement device 112, e.g., using touch screen 114, and into POCED 130 using touch screen 134. Measurement state information also has been in POCED 130, for example, such as date and time from POCED clock and calendar, and such as geographic information provided by the POCED internal GPS. Portions of the measurement state information also may reside in remote system 140, which may be called or obtained interactively by POCED 130. This may include, for example, altitude, ambient temperature, local weather, and so on.

After the App (at 600) automatically pulls certain parameter data from the POCED, such as the user, the test, the date and time, and the location, in a first step, (at 602), the App analyzes the time to determine whether the currently-planned test will be conducted within the permissible time window, e.g., morning hours between 7 am and 9 am. If the current time is outside the time window, the App (at 604) causes the touch screen 134 to display a message indicating that the test is outside the time window, and stops, optionally suggesting to the user with through the display that the test be conducted the next day. If at 602 the App determines that the current time is within the allotted time window, it moves to 606 and displays a query asking the user whether he or she had had any food or clinks (other than water) since waking The user responds by making the appropriate input at touch screen 134. If the response to the query at 606 is no, the App at 608 presents another query, asking if the user has exercised that morning. If the response again is no, then the App (at 612) proceeds to initiate the ketone measurement test.

Returning to the query at 606, if the user's response is yes, then the App (at 614) presents a query asking the user to designate whether the user had food, a beverage or both. If the response is food or both food and a beverage, processing by the App continues to 616, where the App presents the user with the display "the test can only be performed and valid results obtained if it is taken on an empty stomach. Please try again tomorrow," at which point the App stops processing (at 618). If the response at 614 had been beverage, then in this illustrative application the App (at 620) would have proceeded to the ketone test, but would recorded the fact the a beverage had been consumed and flagged the associated measurement result for compensation.

Communication Paths

Given the flexibility afforded to preferred systems and methods within the present invention, there are multiple possible communication paths and processes among the various principal components, including between the measurement device and communications device, and between the communications device and the remote system.

The measurement device preferably provides the measurement signal to the communications device promptly upon generating it. If the measurement device performs analysis or compensation, the transmission may be of the modified measurement signal, or it may comprise the measurement signal and the associated analysis or compensation data as separate data components. The measurement device also preferably transmits measurement device data and measurement data, in full form or as a confirmation, change indication, etc., as discussed herein above.

The transmittal of the measurement signal by the measurement device alternatively may be after according to a pre-determined schedule, upon the occurrence of a discrete action event, or the like. The pre-determined schedule may be at a fixed time each day, on a predetermined day and time each week, etc. Examples of transmission upon the occurrence of a discrete action or event would include transmission upon, and in response to, a signal from the communications device requesting the transmission, or indicating that the communications device is standing by for receipt of the measurement signal. The event triggering transmission also may comprise one or more environmental factors, for example, upon leaving home in the morning.

The communications device similarly may transmit the measurement signal and optionally associated data to the remote system automatically without external instruction, e.g., from the user, according to a pre-determined schedule, upon the occurrence The transmittal of the measurement signal may either be after a discrete action, for example, after performing a test using the breath analysis device, or at scheduled internals, for example, every day in the morning, or at a nondeterministic time subject to environment factors, for example, the breath analysis device may not be able to contact the remote system to transmit data and thus will cache the data internally until a connection can be established.

In many preferred systems, depending on the specific application and system and method objectives, the measurement device automatically and mandatorily transfers the measurement signal to the communications device, and the communications device automatically transfers that measurement signal on to the remote system. These transfers are automatic in the sense they occur without requirement for any input, authorization or other action by a user. The devices themselves make the transfers.

Optionally but in many embodiments preferably, this "mandatory uplink" feature is combined with a "user report withholding" feature, in which the measurement signal is transmitted directly and automatically from the measurement device to the communications device and automatically on to the remote system, but while withholding the measurement signal from the user. The remote system then analyzes the measurement signal, alone or in conjunction with one or more compensation factors that have been generated and/or applied at any of the three principal system components—the measurement device, communications device and remote system—and authorizes or withholds authorization for the disclosure of the measurement signal to the user. If the remote system authorizes the disclosure, this authorization is communicated to the communications device, and optionally to the measurement device, whereupon the measurement signal is displayed and thus disclosed to the user. In instances wherein authorization for disclosure is withheld, this also preferably is communicated to the communications device, whereupon an appropriate notice is provided to the user. The communications device or the measurement device then optionally may query the user, e.g., to obtain information to address measurement signal anomalies, parameter data anomalies, obtain additional parameter data, etc. The combination of these mandatory uplink and withholding features can be advantageous for multiple reasons. As an example, the remote system may be consulted to improve the measurement process (e.g., use different parameters given a user's response). This response signal or information can be useful, for example, in subsequent measurements to control or modify an operating parameter for instrumentation within the measurement device, e.g., such as to control or adjust a fluid pump, control a linear actuator, adjust sensors parameters such as the flow rate of the fluid through the sensor, and so on. For example, where the measurement device includes a pump that pumps the ketone-containing fluid sample through a colorimetric sensing system that uses a developer solution, the operating or processing parameters that may be adjusted. Illustrative ranges of adjustment are shown in Table 3.

TABLE 3

Illustrative Operating and Processing Parameter Adjustments

| Operating Parameters | Low Range (LR) | Mid- Range (MR) | High- Range (HR) |
|---|---|---|---|
| Pump speed | 40 sccm | 60 sccm | 80 sccm |
| Pump time | 120 sec | 80 sec | 40 sec |
| Development time | 90 sec | 90 sec | 15 sec |
| Processing Parameters | | | |
| Raw data analysis methodology | Equilibrium | Equilibrium | Kinetic |
| Analysis algorithm | Mid-point color analysis | Mid-point color analysis | Differential signal analysis |

In Table 3, "sccm" is standard cubic centimeters per minute, and "sec" is seconds. The development time is the time period during which the developer solution contacts the ketone in the sensor. The raw data analysis methodology is the method by which the raw data is computationally analyzed so as to be useful to convert to a concentration level, and can be adjusted between an "equilibrium" methodology (i.e., determining the raw signal level once the signal is generally not changing), and a "kinetic" methodology (i.e., analyzing the raw signal based on the slope or other characteristic as it is rapidly changing).

As a further example of its potential benefits, mandatory uplink can be useful to ensure that parameter data is stored and made available to facilitate broader population data.

In many presently preferred system embodiments and methods, a system of communications transfers between the principal system components occurs to provide beneficial features such as greater efficiency, greater security, and enhanced capability. According to this system of transmissions, component "handshaking" occurs to ensure that the transmission target is ready to receive the transmission, data spread throughout the system can be searched, parsed, shared, etc., processing tasks can be allocated, receipt confirmations can be provided, and the like.

As noted herein above, the parameter data and population data can take a number of forms, and can vary considerably in terms of its volume, organization, and the like. Population data, for example, may be in succinct form, for example, such as statistical parameters for a clinically-evaluated measurement variable, a demographic variable, or the like, but in some instances may comprise relatively voluminous raw or compiled data. In some applications, although the data may not necessarily be voluminous, it may be difficult to search and require relatively intensive processing to conduct needed searches.

The storage and processing capacities of some components, e.g., the measurement device, in certain applications may be substantially more limited than those of the communications device. Similarly, the storage and processing capacities of the remote system may be substantially greater than those of the measurement device or the communications system. Accordingly, in preferred embodiments in which a more sophisticated, secure and robust system is desired, one may apportion some data, e.g., essential measurement device data and measurement data and user- or user-entered measurement state data, at the measurement device, other data, e.g., relatively limited data filters and relatively limited parameter data, at the communications device, and still other data, e.g., complex and/or voluminous parameter and population data and more complex data filters, at the remote system. In such systems, for example, upon making the ketone measurement, the measurement device automatically transfers the measurement signal, the limited measurement device and measurement data and the measurement state data to the communications device. The communications device analyzes this data with pre-stored data filters, determines what parameter and/or population data are required to generate and apply appropriate compensation factors, and consults its pre-stored data and processing capability to ascertain whether the communications device possesses the necessary data and processing capability to undertake the appropriate compensation factors generation. If it determines additional data is needed, the communications device transmits a data request to the remote system, whereupon the remote system collects and transmits the requested data to the communications system. The communications system then can use the full set of data it now possesses to undertake the processing to generate and apply the compensation factors. The communications system then displays the modified or compensated measurement signal for the user. It also preferably transmits the signal to the remote system for storage, further analysis, notice, etc.

If during its processing the communications system or the remote system determines that the processing capability of the communications device is inadequate for the processing tasks at hand, the remote system transmits an instruction to the communications device indicating that the processing will take place at the remote system and the modified measurement signal will then be forwarded to the communications system.

Independently of the transmission mode or modes as described immediately above, the measurement device and/or the communication device may and preferably do retain a local copy of the transmitted data such that the data resides both on the remote system as well as the measurement device or the communications device or both.

This retention of transmitted data in multiple locations may be motivated by any combination of several reasons, depending on the specific application. As an example, the remote system may be inaccessible due to schedule maintenance, service outage, capacity limitations or other forms of communication disruption. In this event, the user will still have access to the data on the measurement device and/or the communications device.

It has been noted and described herein above that the software App can be and preferably is interactively engaged with the user. Examples of commands to the user that the App can provide in preferred implementations of the App are set forth in Table 4.

TABLE 4

| | Examples of Command User |
|---|---|
| A | Recalibrate your device |
| B | Start using the device in the morning |
| C | Please sit down and relax for 10 minutes before using the device |

The App also can provide useful information or feedback to the user. Examples of such feedback are set forth in Table 5. To exemplify the utility and benefits of this feature, consider the following example. Individuals can increase their level of fat metabolism by exercising, which will cause breath acetone levels to be elevated. On the other hand, ovulation results in a slightly elevated body temperature, which in turn causes enhanced fat metabolism. Therefore, for female users, a normalized compensation factor for breath acetone may take into account the day of that woman's menstrual cycle. This may enable the woman to compare how much fat she has metabolized on account of her exercise program between Day 1 and 14 without interference from enhanced metabolism caused by the ovulation.

TABLE 5

| | Examples of User Feedback from App to User |
|---|---|
| A | Speak with your physician about decreasing the amount of medication XYZ that you are currently taking |
| B | See your physician immediately - critical values were identified |
| C | Your new "target" value should be 15 (instead of 20) |
| D | Your new "target" value should be 20 (instead of 15) |
| E | Purchase a cartridge for breath analyte isoprene and perform that measurement simultaneously with your current test. Your results will now be reported as a ratio |
| F | Input your urine pH at the start of each test |
| G | Increase the amount of resistance training that you currently perform |
| H | Begin taking Vitamin D |
| I | Your values will begin to drop soon - but do not worry, they will likely increase again in 7-10 days |

EXAMPLES

In view of the foregoing, the following examples, undertaken for these illustrative purposes using the ketone measurement systems described herein above and implementing presently preferred method implementations including the App, will illustrate how the inventive systems and methods can be used to compensate for variability inherent in ketone measurements and substantially improve such measurement results.

Example 1

Figure 12:
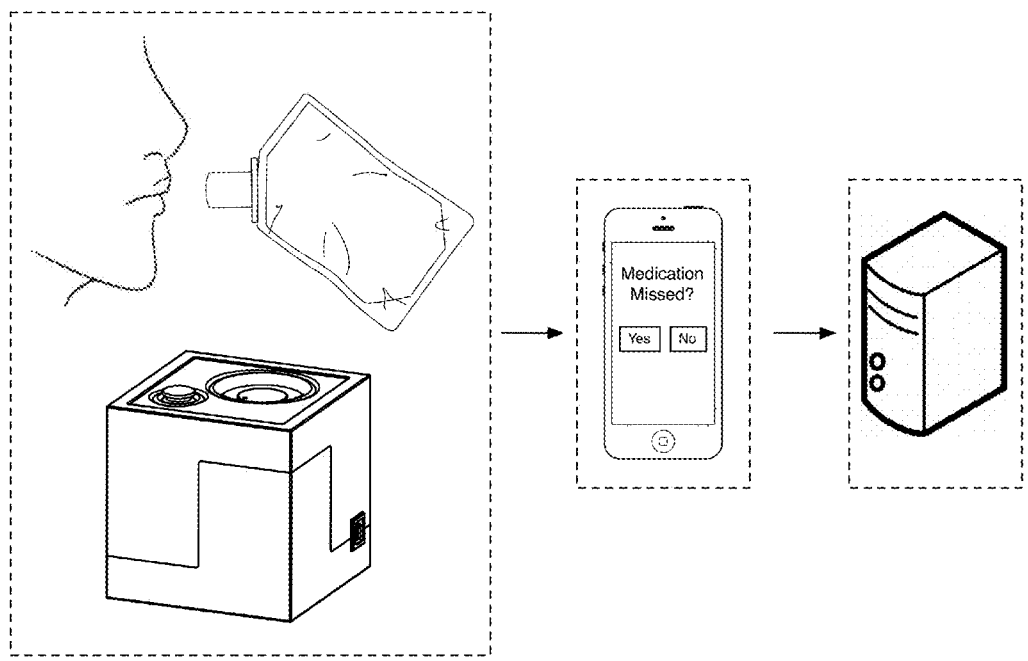
FIG. 12 shows a system for measuring ketones in the breath of a user in accordance with a presently preferred embodiment of another aspect of the invention.

Many potential users of a ketone home monitor are presently taking metabolically-impactful medications, such as beta-blockers. In clinical studies, the assignee hereof has observed ketone levels (in breath, blood and urine) to increase in response to missed doses of certain anti-lipolytic medications such as beta-blockers. In other words, when a patient regularly takes the beta-blocker, his or her ketone levels are relatively lower than they otherwise would be. Accordingly, if he or she misses a dose, the measured ketone levels normally would be higher than if they had not missed the administration of the medicine. Insulin is another medication that decreases ketone levels. In contrast, certain medication such as phenteramine (or other weight loss stimulators) appear to cause an increase in ketone levels. Thus, in order to accurately track and trend ketone levels for a given user, it is useful and potentially important to determine if, on a given day, the user inadvertently missed his or her medication. Systems and methods according to aspects of the invention as described herein provide for such tracking, and for appropriate compensation to offset the aberrant effects in the measurement results. An example of such a system is shown in FIG. 12.

In this example, the user undertakes a 13-day ketone measurement plan in which he tests her blood, urine and breath for each of 13 consecutive days. The user used system 210 for blood measurement, and at essentially the same time each day used system 310 for urine ketone measurement and system 510 for breath measurement. The ketone measurement results for each of these tests over the 13-day period is shown in Table 6.

TABLE 6

Ketone Measurement Results in Example 1

| Date | Blood | Urine | Breath |
|---|---|---|---|
| Day 1 | 0.2 | 5 | 1.3 |
| Day 2 | 0.2 | 5 | 2.0 |
| Day 3 | 0.2 | 5 | 2.6 |
| Day 4 | 0.2 | 5 | 2.4 |
| Day 5 | 0.3 | 5 | 5.4 |
| Day 6 | 0.3 | 5 | 1.6 |
| Day 7 | 0.2 | 5 | 5.1 |
| Day 8 | 0.4 | 40 | 9.1 |
| Day 9 | 0.3 | 5 | 2.1 |
| Day 10 | 0.3 | 5 | 7.7 |
| Day 11 | 0.3 | 5 | 3.8 |
| Day 12 | 0.2 | 5 | 2.4 |
| Day 13 | 0.3 | 15 | 4.2 |

To compensate for the missed dose, the App searches for a first missed dose from the given user. In the data set presented above, the level from Day 7 to Day 8 increased in breath by 4 ppm and increased by 35 in urine.

Accordingly, for this user, given that medication impacts are highly user-specific (given the dosage differences and individual pharmacogenomic responses), in this case, the App relies on data collected from this individual user (e.g., a compensation factor of decreasing by 4 ppm in breath or decreasing by 35 mg/dL in urine) to adjust future situations of missed doses of propanalol.

This individual missed her Propanol (anti-lipolytic) medicine on the evening of Day 7. Note the substantially higher levels on Day 8.

The application of a compensation factor may happen in real-time or it may be post-processed. The algorithm employing the compensation factor, in this case the missed dose of medication, would likely be a software plug-in to the overall application. In this example and in the context of personalized medicine, if the user had not missed a dose, there would be no way for the software to correct for this factor. Consequently, after the second instance in which the user missed the dose, a compensation factor would be determined or confirmed and would then be applied in a post-processing fashion to historical data.

In other words, the data shown in the plot may change over time as additional measurement data is collected. This would result in raw data, a first processed result and a second processed result (after the measurement is refined based on additional data that is collected). The user may have access to the raw (unprocessed) result, the first processed result and the second processed result, or some subset thereof.

Example 2

Sleep interruption can change ketone levels, and thus sleep soundness is a variable for which a compensation factor may be constructed and applied. Consider this example to illustrate. In a 14-day program to measure ketone levels in a user's blood, urine and breath, the user used system 210 for blood measurement, and at essentially the same time each day used system 310 for urine ketone measurement and system 510 for breath measurement. The ketone measurement results for each of these tests over the 14-day period is shown in Table 7.

TABLE 7

Ketone Measurement Results in Example 2

| Date | Blood | Urine | Breath |
|---|---|---|---|
| Day 1 | 0.4 | 5 | 2.9 |
| Day 2 | 0.7 | 15 | 9.4 |
| Day 3 | 0.3 | 15 | 3.0 |
| Day 4 | 0.4 | 15 | 18.5 |
| Day 5 | 0.7 | 25 | 13.1 |
| Day 6 | 0.6 | 25 | 13.0 |
| Day 7 | 2 | 60 | 51.1 |
| Day 8 | 0.4 | 25 | 11.5 |
| Day 9 | 0.3 | 5 | 4.3 |
| Day 10 | 0.9 | 60 | 6.2 |
| Day 11 | 0.5 | 40 | 13.6 |
| Day 12 | 1.3 | 40 | 12.8 |
| Day 13 | 0.1 | 5 | 2.9 |
| Day 14 | 0.6 | 15 | 6.4 |

To establish a baseline, the average of the measured blood ketone levels for Days 1 to 6 was 0.5 mM. The average for Days 8 to 12 was 0.68 mM. A data filter in the App checks measured level consistencies and trends from day to day, and detected an abnormally high level on Day 7. Admittedly this likely would be an exaggerated or even extreme case. Having detected this unusually high level, the App prompted the user to explain that high level. It was found upon inquiry with the user that he experienced abnormal sleep during the night between Days 6 and 7. The user reported no abnormal sleep or other factors between Days 1 to 12, other than isolated sleep on Day 7.

The user addressed this hypothesis that abnormal sleep caused the variation by creating a factor: "Abnormal Sleep" in the App. Working with his nutritionist, the following compensation factor was created:

$$2\text{ mM} - 0.68\text{ mM} = 1.32\text{ mM}. \quad \text{Compensation Factor}$$

In future days where this individual has experienced interrupted sleep, e.g., due to a stressful presentation the next morning, which occurrence was inputted into the App, the App subtracted 1.32 mM from his measured blood ketone levels. This algorithm makes use of past, current and "future" or subsequent data in order to create a compensation factor.

This algorithm was also something that was identified by the software (instead of the medication example which was a built-in plug-in).

Example 3

The age of a user can impact ketone concentrations and thus ketone measurement. Increasing age is generally associated with declining productivity, decreasing energy generation, and decreasing or relatively lower blood, urine and breath ketone concentrations. A compensation factor can correct for variance in expected activity and performance levels due to confounding variables, such as age.

Figure 13:
FIG. 13 shows a hypothetical correlation between user age and average ketone concentrations in a body fluid, which correlation is used to illustrate a presently preferred method implementation according to another aspect of the invention.

FIG. 13 shows a hypothetical correlation between user age and average ketone concentrations in a body fluid, which correlation is used to illustrate a presently preferred method implementation according to another aspect of the invention.

Example 4

Luminal inflammation may affect absorption of, in this case, metabolites. The amount and type of metabolites absorbed impacts metabolites available for energy production. For instance, if byproducts of fat metabolism are absorbed by the lumen instead of being released into the blood stream, this will correspondingly decrease acetone production in breath. A compensation factor can correct for inflammation in the gut.

Example 5

Compensation factors typically are specific for different conditions. For instance, when acetoacetate is produced in the body, it can be converted into β-HB or acetone. Some of the acetone production is spontaneous, but other production is facilitated by acetoacetate decarboxylase. If acetoacetate decarboxylase is deficient or otherwise exhibiting reduced activity, this may reduce the amount of acetone present in breath, even though acetoacetate and β-HB (both ketones and reflective of fat metabolism) are still present.

The methodology described above can be applied to a range of analytes, for example, such as ammonia, instead of or in addition to testing acetone (or some other analyte) in the same device.

Example 6

Figure 14:
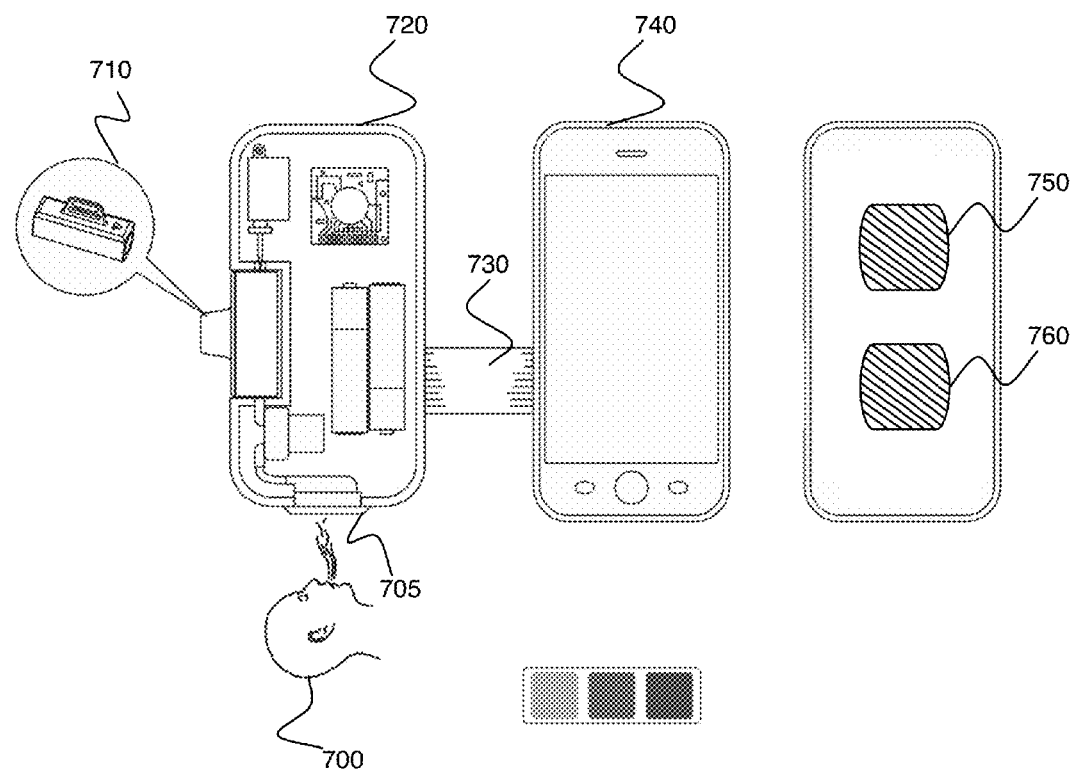
FIG. 14 shows a ketone measurement device that includes a heart rate monitor used to illustrate presently preferred methods according to aspects of the invention.
Figure 15:
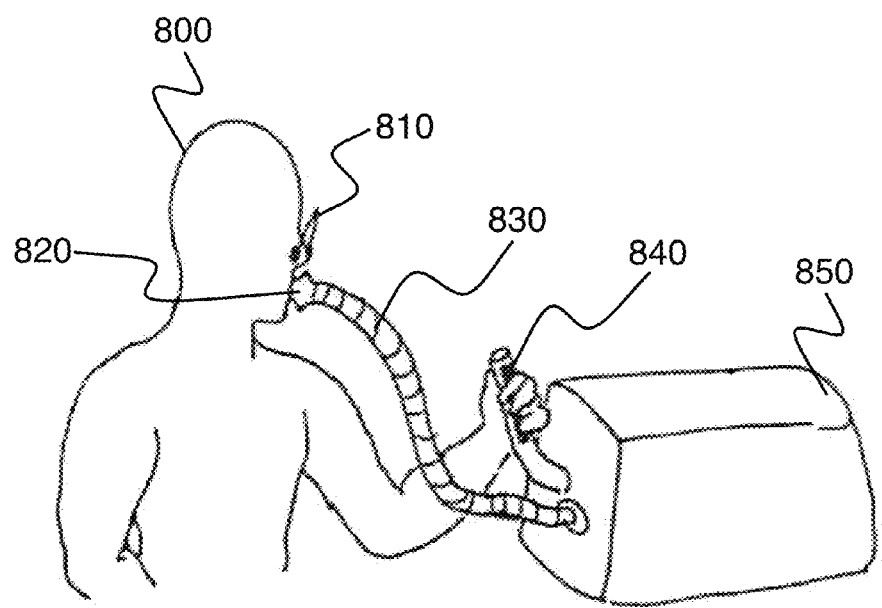
FIG. 15 shows another ketone measurement device that includes a heart rate monitor used to illustrate presently preferred methods according to aspects of the invention.

FIGS. 14 and 15 present breath analysis devices with integrated heart rate monitors. Breath analytes are exhaled from alveolar air space. Analyte levels can be artificially low in the event that a user is hyperventilating, suggesting that there is insufficient time for equilibration between the blood and the gas in the alveolar air of the lungs. It is consequently desirable to assess the patient's respiratory state, and heart rate facilitates this.

FIG. 14 shows a hand-held embodiment of a cell-phone enabled breath analysis device with an integrated heart rate monitor. Here, the user 700 exhales through a mouthpiece 705 into a sensor 710 that is coupled to the cell phone 720. During the measurement process, the user's hands are attached to the heart rate monitors 750 and 760 affixed to the back of the cell phone.

In FIG. 15, the user (800) exhales into a breath analysis device (850) through a mouthpiece (820). In FIG. 14, the user's hand is affixed to a heart rate monitor (840). Additionally, there are instances in which to collect a breath sample void of interferents and that best reflects the internal user physiology, the user's nasal passage should be blocked with a nose clip 810 and the user should exhale multiple times through a rebreathing cord 830 until such a time as the heart rate is stable.

Example 7

Disease or other conditions that alter any step or contributor to a step in the citric acid cycle can impact the efficiency with which energy is produced from any one or a combination of carbohydrate, protein, and fat substrates. Breath levels can be adjusted with a compensation factor that accounts for known deficiencies.

Example 8

In clinical studies that the present assignee has performed, it has observed that after several week of being in a state of nutritional ketosis, urinary excretion of ketone bodies declines for certain individuals. This is consistent with the phenomenon of renal conservation.

To simulate the effect of renal conservation in individuals who are in a state of ketosis for a prolonged period of time (e.g., more than six months), a starvation model is used. In six weeks of starvation (potentially equivalent to 6 months of ketosis), acetoacetate in the urine drops by a factor of 5/8.

As such, the software App in system 310 (FIG. 6) includes a starting compensation factor for keto-adapted individuals of 5/8 after an individual has been on a low-carb diet for six months. In other words, if the sensor 318 measures a level of 80 mg/dL for urine ketones in week 1, the system adjusts this level to 50 mg/dL.

As time goes on and system 310 is used by more individuals, increasing data will be aggregated. Instead of the starvation-mode-driven data, actual data for individuals who are keto-adapted can be collected. This algorithm, instead of being driven by a hard-coded value, can then driven by Population Data.

Figure 16:
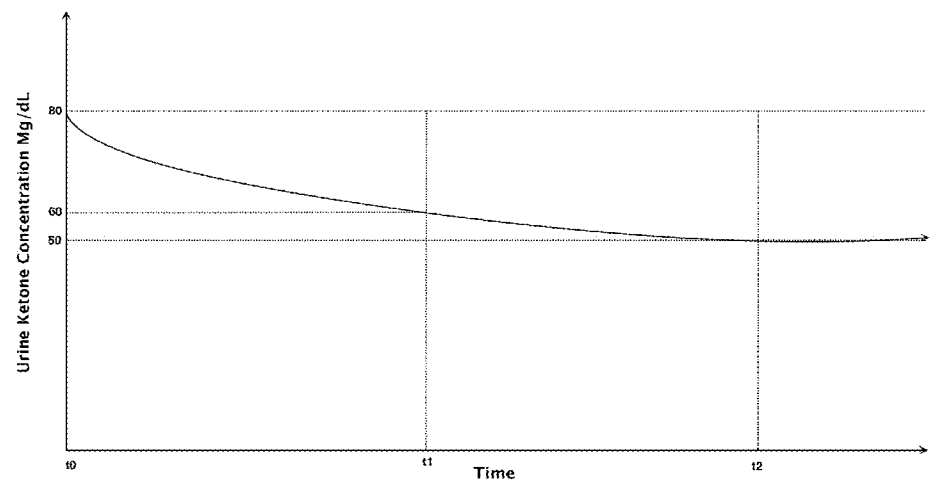
FIG. 16 shows a hypothetical correlation between time and urinary ketone concentrations, which correlation is used to illustrate a presently preferred method implementation according to another aspect of the invention; and, FIG. 17 shows a system for measuring one or more ketones in the blood of a user in accordance with a presently preferred embodiment of another aspect of the invention.

FIG. 16 shows a hypothetical correlation between time and urinary ketone concentrations, which correlation is used to illustrate a presently preferred method implementation according to another aspect of the invention.

Based on this, the App in this illustrative example would apply compensation to adjust the declining or ultimately declined level to a "normal" level to fully compensate for the elevated ketone and ketoadaptive states. This could be done by applying a varying compensation factor that increased in value as the urine ketone levels drop, until t2, at which time a steady or constant value compensation factor would be applied. The compensation factor in general terms would be a ratio of the "normal" ketone level (here 80 ml/dL) over the actual measured ketone level. At time t0, CF would be zero. At time t1, CF=80/60=1.3. At time t2, CF=80/50=1.6. The intermediate values would range according to the normal and measured values, and would be a function of the slope or derivative of the ketone concentration curve as a function of time.

Example 9

Diabetic ketoacidosis is a form of metabolic acidosis. In response to metabolic acidosis, the body may compensate by respiratory alkalosis. More specifically, the normal carbon dioxide levels in exhaled human breath is about 5% by volume. For people in metabolic acidosis, the buildup of ketones in the blood increases acidity and lowers pH to below its normal level of about 7.4. The body naturally tries to compensation to raise and thus rebalance the pH by converting carbon dioxide to alkaline carbonates. In the process, the carbon dioxide concentration in lungs is raised from the normal 5% level to about 8&, which represents a 60% increase. The person responds to this substantially increased CO2 level by breathing rapidly and deeply, hyperventilating, in an attempt to clear the lungs of the CO2 laden air and restore fresh oxygenated air. This hyperventilation also causes a volumetric dilution factor.

If it is desired to measure the person's breath acetone levels while in this state, it is expected that the measured acetone concentrations will be lower from these effects, and the reduction may be approximated by the increase in carbon dioxide partial volume. Accordingly, a compensation factor of 60% would be applied to the measured breath acetone value obtained from system 410 or 510 for this user while in this state.

Example 10

User A and User B are in identical physical condition (e.g., same height, same weight, same ethnicity, same gender, same health status, etc.) except that User B has chronic obstructive pulmonary disease (COPD) and User A does not. User B's airways are restricted, and this restriction causes a diffusion barrier to transport from the blood stream to breath. This diffusion barrier is expected to cause a decrease in the aggregate breath analyte released, or it require more time for release. Each user provides a breath sample by exhaling under otherwise identical protocols and circumstances into a respective Tedlar bag such as bag 516b of system 510 (FIG. 9) with one-way value 516d, and breath acetone measurement device 512 is used with both samples. Such measurement yielded measured levels of 200 ppb for User A and 120 ppb for User B. Measurement device 512 automatically transmits these measured values POCED 530, which automatically transmit them to the central facility 542, where it is incorporated into remote system 540 and its associated processor.

Based on analysis of users of similar age and physical condition with and without CPD, parameter information is obtained and stored in remote system 540, indicating that users with COPD on average have an 80% blockage of the airway, and correspondingly parameter data in the form of a compensation factor of normal airway flow rate plus the 80% blockage (i.e., 1=0.80) would be applied to future measured values to compensate for the COPD-related obstruction.

Accordingly, the following processing and adjustment is made at the central facility:

Breath Level*(1+"% Airway Blockage")=Compensated Levels 200 ppb*(1+0%)=200 ppb  User A:

120 ppb*(1+80%)=216 ppb  User B:

There are a variety of specific factors that can be addressed using such compensation methods and factors. The following examples illustrate this.

As has been noted, devices, systems and methods according to the various aspects of the invention as disclosed herein provide substantial flexibility in the predisposition, storage or placement of data and information needed for or relevant to the modification or adjustment of analyte measurement data. They advantageously provide the mechanism and means to significantly and in some cases greatly improve the accuracy and reliability of breath analyte measurements.

The comments herein above regarding the "user" of measurement unit 11 also apply to the user of the other preferred embodiments presented herein, e.g., including embodiments that comprises separate ketone measurement devices and communications devices. The person whose ketones are being measured may or may not also comprise the person who operates the devices. For ease of illustration, they are assumed to be one and the same for purposes of the illustrative examples provided herein, but this is not necessarily limiting.

The comments herein above regarding the size and portability features of measurement unit 11 and optional locations for use also apply to the other preferred embodiments presented herein as well.

Variations in the detailed embodiments and implementations as specifically disclosed herein are possible within the scope of the invention. As has been disclosed herein above, for example, a variety of parameters and factors may be used. The specific ones used in a given application or design will depend among other things on the analyte and correlated physiological or pathophysiological state being considered, the availability of parametric data or information, the sophistication and cost of the system, the nature and condition of the user, and so on. The pre-disposition of parametric data or information between the breath analysis device and the remote system or databases also can be highly flexible and adaptive. Similarly, the processing to obtain the compensation factors or adjustment information can be flexibly centered at the breath analysis device, the remote system, or it may be distributed between or among them. The manner of providing the adjusted analyte measurement between the device and remote system and to other potential distributees, and the timing of such distribution, conditions on them, etc., also are quite flexible with these devices, systems and methods.

What is claimed is:

1. A system for measuring a ketone in a breath of a user, the system comprising:
    a portable ketone measurement device that measures the ketone at a first location and generates a measurement signal indicative of the concentration of the ketone in a breath sample of the user, the portable ketone measurement device comprising a pump that moves the breath sample along a flow path to a ketone sensor, and comprising a wireless transceiver capable of wirelessly transmitting the measurement signal;
    a communications device located at the first location, the communications device configured to receive a wireless transmission of the measurement signal from the portable ketone measurement device, and to transmit the measurement signal; and
    a remote system disposed at a second location remote from the first location that receives the measurement signal from the communications device;
    at least one of the portable ketone measurement device, the communications device and the remote system comprising at least one processor that processes parameter data and generates a compensation factor for effecting a modification of the measurement signal to compensate for at least one of the following: (1) an age of the user, (2) a nutritional ketosis condition of the user, (3) a chronic obstructive pulmonary disease (COPD) condition of the user, (4) a missed medication event by the user, (5) an interrupted sleep condition of the user, (6) a diabetic ketoacidosis condition of the user.

2. A system as recited in claim 1, wherein the communications device comprises a smart phone.

3. A system as recited in claim 2, wherein the smart phone comprises a processor that is programmed to process the parameter data to obtain the compensation factor.

4. A system as recited in claim 1, wherein the parameter data comprises user-specific data.

5. A system as recited in claim 4, wherein the user-specific data comprises at least one of lifestyle data, physical data and pathophysiological data.

6. A system as recited in claim 1, wherein the remote system comprises storage that pre-stores a portion of the parameter data.

7. A system as recited in claim 6, wherein the remote system storage pre-stores the portion of the parameter data in the form of population data.

8. A system as recited in claim 1, wherein the portable ketone measurement device automatically transmits the measurement signal to the communications device upon generation of the measurement signal.

9. A system as recited in claim 1, wherein the communications device automatically transmits the measurement signal to the remote system upon receiving the measurement signal from the portable ketone measurement device.

10. A system as recited in claim 1, wherein the portable ketone measurement device comprises a breath input port configured to connect to a breath sample container.

11. A system as recited in claim 1, wherein the compensation factor is generated based on an age of the user.

12. A method of generating ketone measurements, comprising:
generating, by a portable ketone measurement device, ketone measurements from bodily fluid samples of a user, each ketone measurement generated by the portable ketone measurement device from a respective bodily fluid sample of the user by analyzing the bodily fluid sample with a ketone sensor, the portable ketone measurement device configured to receive an insertable component containing a bodily fluid sample; and
by execution of program code by one or more processors:
recording, in connection with some, but not all, of the ketone measurements, occurrences of a user condition that can affect ketone measurements;
determining, by analyzing the ketone measurements in conjunction with the recorded occurrences of the user condition, an amount by which the user condition causes the ketone measurements of the user to vary;
determining that a particular ketone measurement generated with the portable ketone measurement device was generated while the user condition was present; and
modifying the particular ketone measurement based on said amount to compensate for the user condition.

13. The method of claim 12, wherein the user condition is a missed medication condition.

14. The method of claim 12, wherein the user condition is an interrupted sleep condition.

15. The method of claim 12, wherein recording the occurrences of the user condition comprises receiving user input via a software application that runs on a communications device that is separate from the portable ketone measurement device.

16. The method of claim 12, further comprising modifying, based on said amount, a previously-generated ketone measurement that was generated prior to determining the amount by which the condition causes the ketone measurements to vary, the previously-generated ketone measurement generated while the user condition was present.

17. The method of claim 12, wherein the one or more processors are separate from the portable ketone measurement device.

18. The method of claim 12, wherein the insert-able component is a breath container.

19. The method of claim 12, wherein the insert-able component is a test strip.

20. A ketone measurement system, comprising:
a portable ketone measurement device configured to generate ketone measurements from bodily fluid samples of a user, the portable ketone measurement device comprising an input port that receives an insert-able component containing a bodily fluid sample, and comprising a ketone sensor that analyzes the bodily fluid samples, the portable ketone measurement device additionally comprising a transceiver capable of communicating the ketone measurements to a communications device associated with the user; and
executable program code that directs a computing device to adjust at least some of the ketone measurements to compensate for a ketone level variation associated with at least one of the following: (1) an age of the user, (2) a nutritional condition of the user, (3) a pulmonary condition of the user, (4) a missed medication event by the user, (5) an interrupted sleep condition of the user, (6) a diabetic ketoacidosis condition of the user.

21. The ketone measurement system of claim 20, wherein the program code directs the computing device to adjust at least some of the ketone measurements to compensate for a ketone level variation associated with an age of the user.

22. The ketone measurement system of claim 20, wherein the program code directs the computing device to adjust at least some of the ketone measurements to compensate for a ketone level variation associated with a nutritional condition of the user.

23. The ketone measurement system of claim 20, wherein the program code directs the computing device to adjust at least some of the ketone measurements to compensate for a ketone level variation associated with a pulmonary condition of the user.

24. The ketone measurement system of claim 20, wherein the program code directs the computing device to adjust at least some of the ketone measurements to compensate for a ketone level variation associated with a missed medication event of the user.

25. The ketone measurement system of claim 24, further comprising executable program code that directs a computing device to learn an amount of the ketone level variation by analyzing ketone measurements of the user, including both (1) ketone measurements associated with missed medication events, and (2) ketone measurements not associated with a missed medication event.

26. The ketone measurement system of claim 20, wherein the program code directs the computing device to adjust at least some of the ketone measurements to compensate for a ketone level variation associated with an interrupted sleep condition of the user.

27. The ketone measurement system of claim 26, further comprising executable program code that directs a computing device to learn an amount of the ketone level variation by analyzing ketone measurements of the user, including both (1) ketone measurements associated with sleep interruption events, and (2) ketone measurements not associated with a sleep interruption event.

28. The ketone measurement system of claim 20, wherein the program code directs the computing device to adjust at least some of the ketone measurements to compensate for a ketone level variation associated with a diabetic ketoacidosis condition of the user.

29. The ketone measurement system of claim 20, wherein the executable program code comprises code of an application that runs on the communications device associated with the user.

30. The ketone measurement system of claim 20, wherein the executable program code runs on the portable ketone measurement device.

31. The ketone measurement system of claim 20, wherein the executable program code runs on a server that receives the ketone measurements from the communications device associated with the user.

32. The ketone measurement system of claim 20, wherein the insert-able component is a breath container.

33. The ketone measurement system of claim 32, wherein the portable ketone measurement device comprises a pump configured to pump a breath sample from the breath container along a fluid path to the ketone sensor.

34. The ketone measurement system of claim 20, wherein the insert-able component is a test strip.

35. A device-implemented method, comprising:
- by a portable ketone measurement device, generating a ketone measurement based on a bodily fluid sample of a user, and wirelessly transmitting the ketone measurement to a mobile communications device associated with the user, wherein generating the ketone measurement comprises obtaining the bodily fluid sample from a fluid sample component that inserts into the portable ketone measurement device, and analyzing the bodily fluid sample with a ketone sensor; and
- by the mobile communications device, automatically transmitting the ketone measurement to a remote computer system while withholding the ketone measurement from the user, and subsequently outputting the ketone measurement to the user in response to receiving an authorization from the remote computer system.

36. The device-implemented method of claim 35, further comprising, by the portable ketone measurement device, the mobile communications device, or the remote computer system, adjusting the ketone measurement to compensate for at least one of the following: (1) an age of the user, (2) a nutritional ketosis condition of the user, (3) a chronic obstructive pulmonary disease (COPD) condition of the user, (4) a missed medication event by the user, (5) an interrupted sleep condition of the user, (6) a diabetic ketoacidosis condition of the user.

37. The device-implemented method of claim 35, wherein the bodily fluid sample is a breath sample obtained from a breath container.

* * * * *

UNITED STATES PATENT AND TRADEMARK OFFICE
CERTIFICATE OF CORRECTION

PATENT NO. : 9,486,169 B1  
APPLICATION NO. : 14/690756  
DATED : November 8, 2016  
INVENTOR(S) : Lubna M. Ahmad Page 1 of 1

It is certified that error appears in the above-identified patent and that said Letters Patent is hereby corrected as shown below:

In the Specification

In Column 25 at Line 15 (approx.), Change "hydroxybutryrate" to --hydroxybutyrate--.

In Column 32 at Line 46, After "waking" insert --.--.

In Column 32 at Lines 62-63, Change "the a" to --that a--.

In Column 37 at Line 6, Change "phenteramine" to --phentermine--.

In Column 37 at Line 53, Change "propanalol." to --propranolol.--.

In Column 37 at Line 54, Change "propanol" to --propranolol--.

Signed and Sealed this  
Eighteenth Day of April, 2017

Michelle K. Lee  
*Director of the United States Patent and Trademark Office*